(12) United States Patent
Levenberg et al.

(10) Patent No.: US 12,304,151 B2
(45) Date of Patent: May 20, 2025

(54) 3D PRINTED BIODEGRADABLE IMPLANTS

(71) Applicant: TECHNION RESEARCH & DEVELOPMENT FOUNDATION LIMITED, Haifa (IL)

(72) Inventors: Shulamit Levenberg, Moreshet (IL); Ben Kaplan, Kiryat Tivon (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 802 days.

(21) Appl. No.: 17/411,373

(22) Filed: Aug. 25, 2021

(65) Prior Publication Data

US 2021/0379838 A1  Dec. 9, 2021

Related U.S. Application Data

(63) Continuation of application No. PCT/IL2020/050212, filed on Feb. 25, 2020.
(Continued)

(51) Int. Cl.
*B29C 64/40*  (2017.01)
*A61B 17/11*  (2006.01)
(Continued)

(52) U.S. Cl.
CPC ............ *B29C 64/40* (2017.08); *A61F 2/0077* (2013.01); *B33Y 10/00* (2014.12); *B33Y 50/00* (2014.12);
(Continued)

(58) Field of Classification Search
CPC ......... A61B 17/1128; A61F 2002/0081; A61F 2002/0086; A61F 2002/0894;
(Continued)

(56) References Cited

U.S. PATENT DOCUMENTS

2010/0240117 A1\*  9/2010  Ying ................... C12N 5/0068
                                                     435/284.1
2017/0135802 A1     5/2017  McAlpine et al.
(Continued)

FOREIGN PATENT DOCUMENTS

CN       105597162 A  *  5/2016  .......... A61L 31/042
EP       3427697 A2      1/2019
(Continued)

OTHER PUBLICATIONS

Saidy NT, Wolf F, Bas O, Keijdener H, Hutmacher DW, Mela P, De-Juan-Pardo EM. Biologically Inspired Scaffolds for Heart Valve Tissue Engineering via Melt Electrowriting. Small. Jun. 2019;15(24):e1900873. doi: 10.1002/smll.201900873. Epub May 6, 2019. PMID: 31058444.
(Continued)

*Primary Examiner* — Jerrah Edwards
*Assistant Examiner* — Jose H. Trevino, III
(74) *Attorney, Agent, or Firm* — The Roy Gross Law Firm, LLC; Roy D. Gross

(57) ABSTRACT

Methods for making an implant scaffold, comprising providing a 3D template generated according to an image of a lesion site, contacting the 3D template with a solution comprising a polymeric precursor, and evaporating the solution, thereby obtaining an implant scaffold, are provided. Further, implant scaffolds, comprising a water-soluble template in the form of a 3D geometrical array and a polymeric material are provided.

11 Claims, 25 Drawing Sheets

Related U.S. Application Data

(60) Provisional application No. 62/809,793, filed on Feb. 25, 2019.

(51) Int. Cl.
| | |
|---|---|
| *A61F 2/00* | (2006.01) |
| *A61F 2/08* | (2006.01) |
| *B29L 31/00* | (2006.01) |
| *B33Y 10/00* | (2015.01) |
| *B33Y 50/00* | (2015.01) |
| *B33Y 80/00* | (2015.01) |

(52) U.S. Cl.
CPC ............ *B33Y 80/00* (2014.12); *A61B 17/1128* (2013.01); *A61F 2002/0081* (2013.01); *A61F 2002/0086* (2013.01); *A61F 2002/0894* (2013.01); *A61F 2230/0069* (2013.01); *A61F 2240/002* (2013.01); *B29K 2995/0056* (2013.01); *B29L 2031/7532* (2013.01)

(58) Field of Classification Search
CPC ........ A61F 2230/0069; A61F 2240/002; A61F 2002/30062; A61F 2002/30948; A61F 2002/30957; A61F 2002/30985; A61F 2/30942; A61F 2/0077; B29K 2995/0056; B29L 2031/7532; A61L 27/58; A61L 2430/30; A61L 2430/32; A61L 2400/08; A61L 27/18; A61L 27/56; B29C 64/40; B33Y 10/00; B33Y 50/00; B33Y 80/00
See application file for complete search history.

(56) References Cited

U.S. PATENT DOCUMENTS

| | | | |
|---|---|---|---|
| 2018/0168811 A1 | 6/2018 | Ranganathan et al. | |
| 2018/0280580 A1* | 10/2018 | Sakamoto | ............... A61L 27/56 |
| 2019/0350720 A1 | 11/2019 | Koffler et al. | |

FOREIGN PATENT DOCUMENTS

| | | |
|---|---|---|
| WO | 2006017845 A2 | 2/2006 |
| WO | 2017062845 A1 | 4/2017 |
| WO | 2018031491 A1 | 2/2018 |

OTHER PUBLICATIONS

Davis O, Merrison-Hort R, Soffe SR, Borisyuk R. Studying the role of axon fasciculation during development in a computational model of the Xenopus tadpole spinal cord. Sci Rep. Oct. 19, 2017;7(1):13551. doi: 10.1038/s41598-017-13804-3. PMID: 29051550; PMCID: PMC5648846.
Shahriari, D. (n.d.). Degradable Microchannel Nerve Guidance Scaffolds for Central and Peripheral Nerve Repair—From Soft to Rigid [PhD Dissertation]. The University of Michigan, Department of Macromolecular Science and Engineering.
PCT International Search Report for International Application No. PCT/IL2020/050212, mailed May 18, 2020, 4pp.
PCT Written Opinion for International Application No. PCT/IL2020/050212, mailed May 18, 2020, 6pp.
Kakinoki S, Nakayama M, Moritan T, Yamaoka T. Three-layer microfibrous peripheral nerve guide conduit composed of elastin-laminin mimetic artificial protein and poly(L-lactic acid). Front Chem. Jul. 18, 2014;2:52. doi: 10.3389/fchem.2014.00052. PMID: 25101261; PMCID: PMC4103079.
Stokols S, Sakamoto J, Breckon C, Holt T, Weiss J, Tuszynski MH. Templated agarose scaffolds support linear axonal regeneration. Tissue Eng. Oct. 2006; 12(10):2777-87. doi: 10.1089/ten.2006.12.2777. PMID: 17518647.
Marcus M, Baranes K, Park M, Choi IS, Kang K, Shefi O. Interactions of Neurons with Physical Environments. Adv Healthc Mater. Aug. 2017;6(15). doi: 10.1002/adhm.201700267. Epub Jun. 22, 2017. PMID: 28640544.
Guest JD, Moore SW, Aimetti AA, Kutikov AB, Santamaria AJ, Hofstetter CP, Ropper AE, Theodore N, Ulich TR, Layer RT. Internal decompression of the acutely contused spinal cord: Differential effects of irrigation only versus biodegradable scaffold implantation. Biomaterials. Dec. 2018;185:284-300. doi: 10.1016/j.biomaterials.2018.09.025. Epub Sep. 19, 2018. PMID: 30265898.
Slotkin JR, Pritchard CD, Luque B, Ye J, Layer RT, Lawrence MS, O'Shea TM, Roy RR, Zhong H, Vollenweider I, Edgerton VR, Courtine G, Woodard EJ, Langer R. Biodegradable scaffolds promote tissue remodeling and functional improvement in non-human primates with acute spinal cord injury. Biomaterials. Apr. 2017;123:63-76. doi: 10.1016/j.biomaterials.2017.01.024. Epub Jan. 25, 2017. PMID: 28167393.
Pawar K, Cummings BJ, Thomas A, Shea LD, Levine A, Pfaff S, Anderson AJ. Biomaterial bridges enable regeneration and re-entry of corticospinal tract axons into the caudal spinal cord after SCI: Association with recovery of forelimb function. Biomaterials. Oct. 2015;65:1-12. doi: 10.1016/j.biomaterials.2015.05.032. Epub Jun. 23, 2015. PMID: 26134079; PMCID: PMC4523232.
Shahriari D, Koffler JY, Tuszynski MH, Campana WM, Sakamoto JS. Hierarchically Ordered Porous and High-Volume Polycaprolactone Microchannel Scaffolds Enhanced Axon Growth in Transected Spinal Cords. Tissue Eng Part A. May 2017;23(9-10): 415-425. doi: 10.1089/ten.TEA.2016.0378. Epub Mar. 31, 2017. PMID: 28107810; PMCID: PMC5444512.
Pawelec KM, Koffler J, Shahriari D, Galvan A, Tuszynski MH, Sakamoto J. Microstructure and in vivo characterization of multi-channel nerve guidance scaffolds. Biomed Mater. Apr. 25, 2018;13(4):044104. doi: 10.1088/1748-605X/aaad85. PMID: 29411711.
Gunatillake PA, Adhikari R. Biodegradable synthetic polymers for tissue engineering. Eur Cell Mater. May 20, 2003;5:1-16; discussion 16. doi: 10.22203/ecm.v005a01. PMID: 14562275.
Levy-Mishali M, Zoldan J, Levenberg S. Effect of scaffold stiffness on myoblast differentiation. Tissue Eng Part A. Apr. 2009;15(4):935-44. doi: 10.1089/ten.tea.2008.0111. PMID: 18821844.
Sabir, M.I., Xu, X. & Li, L. A review on biodegradable polymeric materials for bone tissue engineering applications. J Mater Sci 44, 5713-5724 (2009). https://doi.org/10.1007/s10853-009-3770-7.
Da Silva D, Kaduri M, Poley M, Adir O, Krinsky N, Shainsky-Roitman J, Schroeder A. Biocompatibility, biodegradation and excretion of polylactic acid (PLA) in medical implants and theranostic systems. Chem Eng J. May 15, 2018;340:9-14. doi: 10.1016/j.cej.2018.01.010. Epub Jan. 3, 2018. PMID: 31384170; PMCID: PMC6682490.
Theodore N, Hlubek R, Danielson J, Neff K, Vaickus L, Ulich TR, Ropper AE. First Human Implantation of a Bioresorbable Polymer Scaffold for Acute Traumatic Spinal Cord Injury: A Clinical Pilot Study for Safety and Feasibility. Neurosurgery. Aug. 2016;79(2):E305-12. doi: 10.1227/NEU.0000000000001283. PMID: 27309344.
Joung D, Truong V, Neitzke CC, Guo SZ, Walsh PJ, Monat JR, Meng F, Park SH, Dutton JR, Parr AM, McAlpine MC. 3D Printed Stem-Cell Derived Neural Progenitors Generate Spinal Cord Scaffolds. Adv Funct Mater. Sep. 26, 2018;28(39):1801850. doi: 10.1002/adfm.201801850. Epub Aug. 9, 2018. PMID: 32595422; PMCID: PMC7319181.
Koffler J, Zhu W, Qu X, Platoshyn O, Dulin JN, Brock J, Graham L, Lu P, Sakamoto J, Marsala M, Chen S, Tuszynski MH. Biomimetic 3D-printed scaffolds for spinal cord injury repair. Nat Med. Feb. 2019;25(2):263-269. doi: 10.1038/s41591-018-0296-z. Epub Jan. 14, 2019. PMID: 30643285; PMCID: PMC6559945.
Shahriari D, Koffler J, Lynam DA, Tuszynski MH, Sakamoto JS. Characterizing the degradation of alginate hydrogel for use in multilumen scaffolds for spinal cord repair. J Biomed Mater Res A. Mar. 2016;104(3):611-619. doi: 10.1002/jbm.a.35600. Epub Nov. 12, 2015. PMID: 26488452.
Braga Silva J, Marchese GM, Cauduro CG, Debiasi M. Nerve conduits for treating peripheral nerve injuries: A systematic literature review. Hand Surg Rehabil. Apr. 2017;36(2):71-85. doi: 10.1016/j.hansur.2016.10.212. Epub Jan. 25, 2017. PMID: 28325431.

(56) References Cited

OTHER PUBLICATIONS

Muheremu A, Ao Q. Past, Present, and Future of Nerve Conduits in the Treatment of Peripheral Nerve Injury. Biomed Res Int. 2015;2015:237507. doi: 10.1155/2015/237507. Epub Sep. 27, 2015. PMID: 26491662; PMCID: PMC4600484.

Guvendiren M, Molde J, Soares RM, Kohn J. Designing Biomaterials for 3D Printing. ACS Biomater Sci Eng. Oct. 10, 2016;2(10):1679-1693. doi: 10.1021/acsbiomaterials.6b00121. Epub Apr. 13, 2016. PMID: 28025653; PMCID: PMC5181796.

Thomas AM, Kubilius MB, Holland SJ, Seidlits SK, Boehler RM, Anderson AJ, Cummings BJ, Shea LD. Channel density and porosity of degradable bridging scaffolds on axon growth after spinal injury. Biomaterials. Mar. 2013;34(9):2213-20. doi: 10.1016/j.biomaterials.2012.12.002. Epub Jan. 2, 2013. PMID: 23290832; PMCID: PMC3552139.

Chia HN, Wu BM. Recent advances in 3D printing of biomaterials. J Biol Eng. Mar. 1, 2015;9:4. doi: 10.1186/s13036-015-0001-4. PMID: 25866560; PMCID: PMC4392469.

Murphy WL, Dennis RG, Kileny JL, Mooney DJ. Salt fusion: an approach to improve pore interconnectivity within tissue engineering scaffolds. Tissue Eng. Feb. 2002;8(1):43-52. doi: 10.1089/107632702753503045. PMID: 11886653.

Shahriari D, Loke G, Tafel I, Park S, Chiang PH, Fink Y, Anikeeva P. Scalable Fabrication of Porous Microchannel Nerve Guidance Scaffolds with Complex Geometries. Adv Mater. Jul. 2019;31(30):e1902021. doi: 10.1002/adma.201902021. Epub Jun. 6, 2019. PMID: 31168865; PMCID: PMC6663568.

O'Brien FJ, Harley BA, Yannas IV, Gibson L. Influence of freezing rate on pore structure in freeze-dried collagen-GAG scaffolds. Biomaterials. Mar. 2004;25(6):1077-86. doi: 10.1016/s0142-9612(03)00630-6. PMID: 14615173.

Kaufman T, Kaplan B, Perry L, Shandalov Y, Landau S, Srugo I, Ad-El D, Levenberg S. Innervation of an engineered muscle graft for reconstruction of muscle defects. Am J Transplant. Jan. 2019;19(1):37-47. doi: 10.1111/ajt.14957. Epub Jun. 29, 2018. PMID: 29856531.

Landau S, Szklanny AA, Yeo GC, Shandalov Y, Kosobrodova E, Weiss AS, Levenberg S. Tropoelastin coated PLLA-PLGA scaffolds promote vascular network formation. Biomaterials. Apr. 2017;122:72-82. doi: 10.1016/j.biomaterials.2017.01.015. Epub Jan. 11, 2017. PMID: 28110114.

Naaman H, Rabinski T, Yizhak A, Mizrahi S, Avni YS, Taube R, Rager B, Weinstein Y, Rall G, Gopas J, Ofir R. Measles Virus Persistent Infection of Human Induced Pluripotent Stem Cells. Cell Reprogram. Feb. 2018;20(1):17-26. doi: 10.1089/cell.2017.0034. PMID: 29412740; PMCID: PMC5804099.

Butts JC, McCreedy DA, Martinez-Vargas JA, Mendoza-Camacho FN, Hookway TA, Gifford CA, Taneja P, Noble-Haeusslein L, McDevitt TC. Differentiation of V2a interneurons from human pluripotent stem cells. Proc Natl Acad Sci U S A. May 9, 2017;114(19):4969-4974. doi: 10.1073/pnas.1608254114. Epub Apr. 24, 2017. PMID: 28438991; PMCID: PMC5441696.

Robinson J, Lu P. Optimization of trophic support for neural stem cell grafts in sites of spinal cord injury. Exp Neurol. May 2017;291:87-97. doi: 10.1016/j.expneurol.2017.02.007. Epub Feb. 9, 2017. PMID: 28189728.

A.A. Szklanny, L. Debbi, U. Merdler, D. Neale, A. Muñiz, B. Kaplan, S. Guo, J. Lahann, S. Levenberg, High-Throughput Scaffold System for Studying the Effect of Local Geometry and Topology on the Development and Orientation of Sprouting Blood Vessels, Adv. Funct. Mater. (2019) 1901335. doi:10.1002/adfm.201901335.

Lu P, Graham L, Wang Y, Wu D, Tuszynski M. Promotion of survival and differentiation of neural stem cells with fibrin and growth factor cocktails after severe spinal cord injury. J Vis Exp. Jul. 27, 2014;(89):e50641. doi: 10.3791/50641. PMID: 25145787; PMCID: PMC4435462.

Koffler, J., Samara, R.F., Rosenzweig, E.S. (2014). Using Templated Agarose Scaffolds to Promote Axon Regeneration Through Sites of Spinal Cord Injury. In: Murray, A. (eds) Axon Growth and Regeneration. Methods in Molecular Biology, vol. 1162. Humana Press, New York, NY. https://doi.org/10.1007/978-1-4939-0777-9_13.

Perry L, Landau S, Flugelman MY, Levenberg S. Genetically engineered human muscle transplant enhances murine host neovascularization and myogenesis. Commun Biol. Oct. 4, 2018;1:161. doi: 10.1038/s42003-018-0161-0. PMID: 30320229; PMCID: PMC6172230.

Luo Y, Lode A, Gelinsky M. Direct plotting of three-dimensional hollow fiber scaffolds based on concentrated alginate pastes for tissue engineering. Adv Healthc Mater. Jun. 2013;2(6):777-83. doi: 10.1002/adhm.201200303. Epub Nov. 26, 2012. PMID: 23184455.

Levenberg S, Rouwkema J, Macdonald M, Garfein ES, Kohane DS, Darland DC, Marini R, van Blitterswijk CA, Mulligan RC, D'Amore PA, Langer R. Engineering vascularized skeletal muscle tissue. Nat Biotechnol. Jul. 2005;23(7):879-84. doi: 10.1038/nbt1109. Epub Jun. 19, 2005. PMID: 15965465.

Ma F, Xiao Z, Chen B, Hou X, Dai J, Xu R. Linear ordered collagen scaffolds loaded with collagen-binding basic fibroblast growth factor facilitate recovery of sciatic nerve injury in rats. Tissue Eng Part A. Apr. 2014,20(7-8):1253-62. doi: 10.1089/ten.TEA.2013.0158. Epub Mar. 17, 2014. PMID: 24188561; PMCID: PMC3993059.

Sussman EM, Halpin MC, Muster J, Moon RT, Ratner BD. Porous implants modulate healing and induce shifts in local macrophage polarization in the foreign body reaction. Ann Biomed Eng. Jul. 2014;42(7):1508-16. doi: 10.1007/s10439-013-0933-0. Epub Nov. 19, 2013. PMID: 24248559.

Ganz J, Shor E, Guo S, Sheinin A, Arie I, Michaelevski I, Pitaru S, Offen D, Levenberg S. Implantation of 3D Constructs Embedded with Oral Mucosa-Derived Cells Induces Functional Recovery in Rats with Complete Spinal Cord Transection. Front Neurosci. Oct. 31, 2017;11:589. doi: 10.3389/fnins.2017.00589. PMID: 29163001; PMCID: PMC5671470.

Shor E, Merdler U, Brosh I, Shoham S, Levenberg S. Induced neuro-vascular interactions robustly enhance functional attributes of engineered neural implants. Biomaterials. Oct. 2018;180:1-11. doi: 10.1016/j.biomaterials.2018.07.001. Epub Jul. 4, 2018. PMID: 30014962.

Han IB, Thakor DK, Ropper AE, Yu D, Wang L, Kabatas S, Zeng X, Kim SW, Zafonte RD, Teng YD. Physical impacts of PLGA scaffolding on hMSCs: Recovery neurobiology insight for implant design to treat spinal cord injury. Exp Neurol. Oct. 2019;320:112980. doi: 10.1016/j.expneurol.2019.112980. Epub Jun. 20, 2019. PMID: 31229638.

Chang GL, Hung TK, Feng WW. An in-vivo measurement and analysis of viscoelastic properties of the spinal cord of cats. J Biomech Eng. May 1988;110(2):115-22. doi: 10.1115/1.3108415. PMID: 3379933.

Shin H, Jo S, Mikos AG. Biomimetic materials for tissue engineering. Biomaterials. Nov. 2003;24(24):4353-64. doi: 10.1016/s0142-9612(03)00339-9. PMID: 12922148.

Sofroniew MV. Dissecting spinal cord regeneration. Nature. May 2018;557(7705):343-350. doi: 10.1038/s41586-018-0068-4. Epub May 16, 2018. PMID: 29769671.

Anderson MA, O'Shea TM, Burda JE, Ao Y, Barlatey SL, Bernstein AM, Kim JH, James ND, Rogers A, Kato B, Wollenberg AL, Kawaguchi R, Coppola G, Wang C, Deming TJ, He Z, Courtine G, Sofroniew MV. Required growth facilitators propel axon regeneration across complete spinal cord injury. Nature. Sep. 2018;561(7723):396-400. doi: 10.1038/s41586-018-0467-6. Epub Aug. 29, 2018. PMID: 30158698; PMCID: PMC6151128.

Rengier F, Mehndiratta A, von Tengg-Kobligk H, Zechmann CM, Unterhinninghofen R, Kauczor HU, Giesel FL. 3D printing based on imaging data: review of medical applications. Int J Comput Assist Radiol Surg. Jul. 2010;5(4):335-41. doi: 10.1007/s11548-010-0476-x. Epub May 15, 2010. PMID: 20467825.

Kakulas, B.A., Lorimer, R.L., Gubbay, A.D. (1998). White matter changes in human spinal cord injury. In: Stålberg, E., Sharma, H.S., Olsson, Y. (eds) Spinal Cord Monitoring. Springer, Vienna. https://doi.org/10.1007/978-3-7091-6464-8_15.

Courtine G, Song B, Roy RR, Zhong H, Herrmann JE, Ao Y, Qi J, Edgerton VR, Sofroniew MV. Recovery of supraspinal control of stepping via indirect propriospinal relay connections after spinal

(56) References Cited

OTHER PUBLICATIONS cord injury. Nat Med. Jan. 2008;14(1):69-74. doi: 10.1038/nm1682. Epub Jan. 6, 2008. PMID: 18157143; PMCID: PMC2916740.

King VR, Alovskaya A, Wei DY, Brown RA, Priestley JV. The use of injectable forms of fibrin and fibronectin to support axonal ingrowth after spinal cord injury. Biomaterials. May 2010;31(15):4447-56. doi: 10.1016/j.biomaterials.2010.02.018. Epub Mar. 4, 2010. PMID: 20206381.

Marom A, Shor E, Levenberg S, Shoham S. Spontaneous Activity Characteristics of 3D "Optonets". Front Neurosci. Jan. 9, 2017;10:602. doi: 10.3389/fnins.2016.00602. PMID: 28119555; PMCID: PMC5220075.

Edri R, Gal I, Noor N, Harel T, Fleischer S, Adadi N, Green O, Shabat D, Heller L, Shapira A, Gat-Viks I, Peer D, Dvir T. Personalized Hydrogels for Engineering Diverse Fully Autologous Tissue Implants. Adv Mater. Jan. 2019;31(1):e1803895. doi: 10.1002/adma.201803895. Epub Nov. 8, 2018. PMID: 30406960.

\* cited by examiner

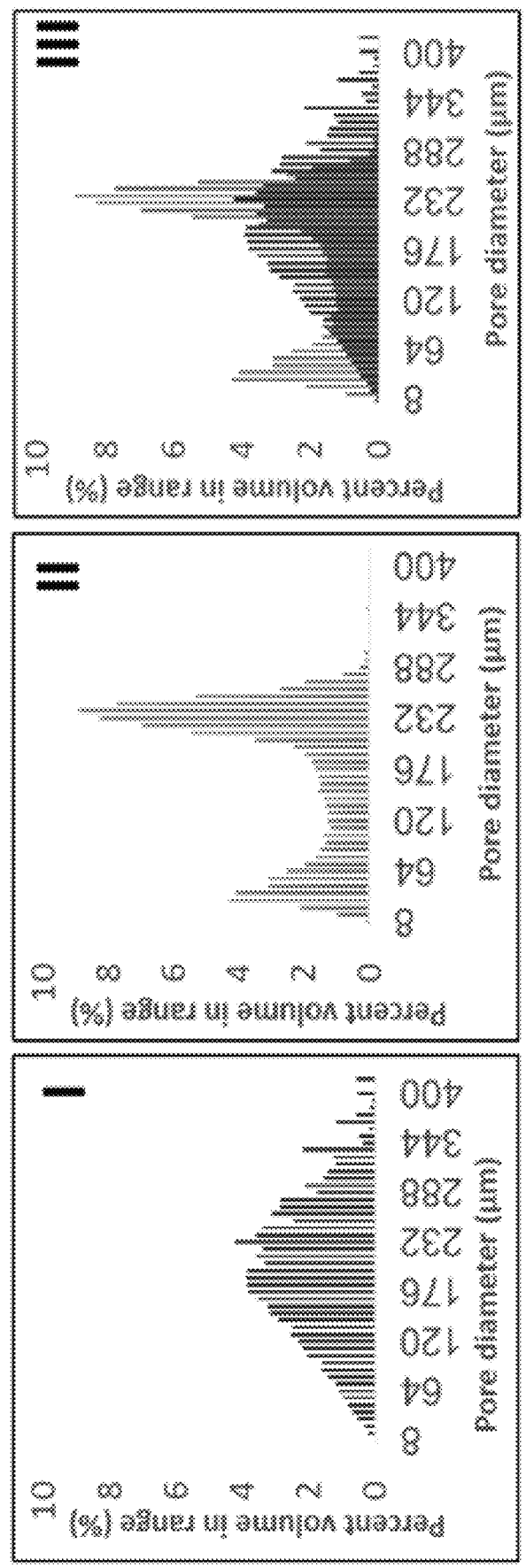
Figure 3G-I
Figure 3G-II
Figure 3G-III

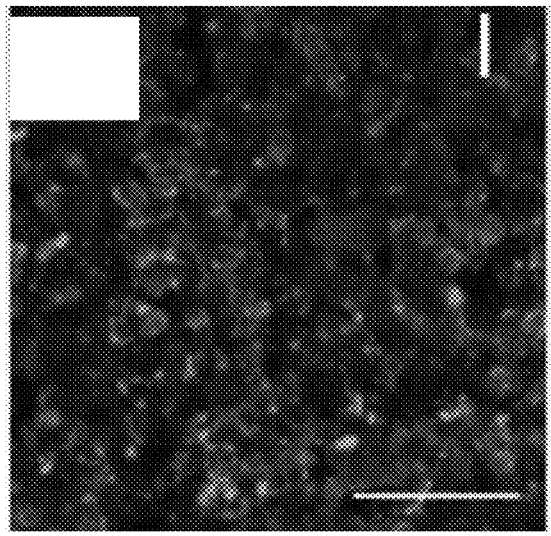 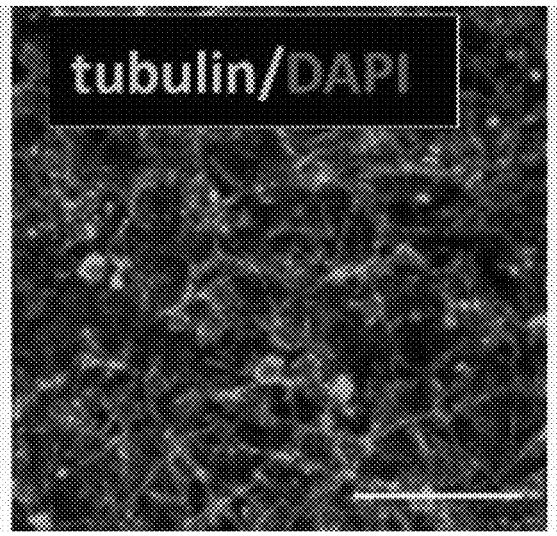
Figure 4D-IFigure 4D-II
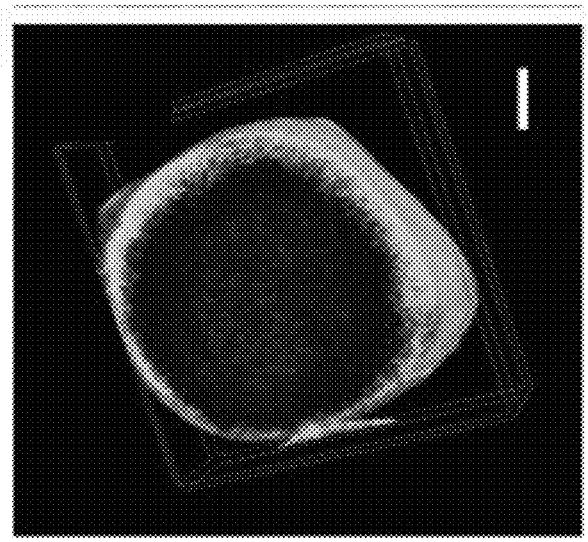 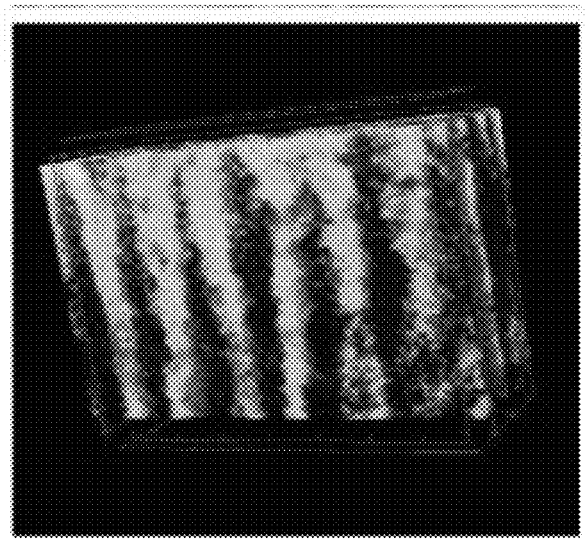
Figure 4E-IFigure 4E-II

3D PRINTED BIODEGRADABLE IMPLANTS

CROSS REFERENCE TO RELATED APPLICATIONS

This application is a bypass continuation of PCT Patent Application No. PCT/IL2020/050212 having International filing date of Feb. 25, 2020, which claims the benefit of priority from U.S. Provisional Patent Application No. 62/809,793, filed on Feb. 25, 2019, entitled "3D PRINTED BIODEGRADABLE IMPLANTS", the contents of which are all incorporated by reference herein in their entirety.

FIELD OF THE INVENTION

The present invention is in the field of material science.

BACKGROUND OF THE INVENTION

After sustaining an injury, severed axons in the spinal cord fail to regenerate. Failure of axonal growth is related to formation of cystic cavities within the injury site. Unlike normal extra-cellular matrix, the cavity does not serve as a permissive substrate onto which axons can attach and grow. Periphery axons have greater potential to regenerate however, also require a permissive growth substrate.

Polymeric scaffolds have been experimentally used in pre-clinical and clinical studies to serve as extra-cellular matrix replacements. Existing polymeric scaffolds are designed by limited fabrication methods that do not allow prototyping of the injury site. The injury site usually has an irregular shape that differs between patients. For maximizing the regeneration process, it is essential that the scaffold will fill the entire lesion cavity. Moreover, current scaffolds are characterized by low porosity which limits cell growth and inaccuracy of topographic cues which limits the guidance of regenerating axons.

SUMMARY OF THE INVENTION

According to one aspect, the present invention provides a method for making an implant scaffold, comprising: a. providing a three-dimensional (3D) template generated according to an image of a lesion site; b. contacting the 3D template with a solution comprising a polymeric precursor, thereby filling a space in the 3D template; and c. evaporating the solution, thereby obtaining an implant scaffold.

In some embodiments, the method further comprises the step (d) of dissolving the 3D template.

In some embodiments, the image of a lesion site is obtained from a magnetic resonance imaging (MRI), X-ray image, a computed tomography (CT) scan, or any combination thereof.

In some embodiments, providing a 3D template comprises printing. In some embodiments, printing is using a micro-bridging pattern technique.

In some embodiments, the 3D template comprises a pattern. In some embodiments, the 3D template comprises aligned geometric forms. In some embodiments, the 3D template comprises parallelly aligned cylinders. In some embodiments, the cylinders have a diameter in the range of 50 μm to 400 μm. In some embodiments, the space in the 3D template is a space between the cylinders. In some embodiments, the space between the cylinders has a thickness in the range of 5 μm to 150 μm.

In some embodiments, the 3D template comprises a water-soluble material. In some embodiments, the 3D template comprises butenediol vinyl alcohol (BVOH), polyvinyl alcohol (PVA), sucrose, lactose, sophorose, or any combination thereof In some embodiments, the polymeric precursor comprises a biodegradable polymer precursor. In some embodiments, the biodegradable polymer precursor comprises poly(lactic-co-glycolic acid), poly(lactic acid), poly(glycolic acid), polycaprolactone, polydioxanone, PVA, polyurethanes, polycarbonates, polyhydroxyalkanoates (polyhydroxybutyrates and polyhydroxyvalerates and copolymers), polysaccharides, polyhydroxyalkanoates polyglycolide-co-caprolactone, polyethylene oxide, polypropylene oxide, polyglycolide-co-trimethylene carbonate, or combinations thereof.

In some embodiments, the solution comprises an organic solvent.

In some embodiments, the solution comprises dioxane.

In some embodiments, the concentration of the polymeric precursor in the solution is 1% to 50% (w/v %).

In some embodiments, the implant scaffold has a porosity of more than 90%.

In some embodiments, the implant scaffold is personalized to a subject.

In some embodiments, the implant scaffold supports neural tissue growth, connective tissue growth, muscular tissue growth, or any combination thereof.

According to another aspect, the present invention provides an implant scaffold prepared according to the method of the present invention, in the form of a 3D geometrical array comprising a polymeric material.

In some embodiments, the 3D geometrical array comprises a plurality of aligned channels having a diameter in the range of 50 μm to 400 μm. In some embodiments, the channels are separated by the polymeric material. In some embodiments, the polymeric material has a thickness in the range of 5 μm to 150 μm.

In some embodiments, the implant scaffold has a total porosity in the range of 90% to 99%.

In some embodiments, the implant scaffold has a Young's modulus in the range of 10 Kpa to 5000 Kpa.

In some embodiments, the polymeric material comprises two biodegradable polymers.

In some embodiments, the implant scaffold is for use in muscle and nerve regeneration.

According to another aspect, the present invention provides an implant scaffold comprising a releasable template in the form of a 3D geometrical array and a polymeric material.

In some embodiments, the 3D geometrical array comprises a plurality of aligned geometrical forms. In some embodiments, the aligned geometrical forms comprise cylinders having a diameter in the range of 50 μm to 400 μm. In some embodiments, the geometrical forms are separated by the polymeric material. In some embodiments, the polymeric material has a thickness in the range of 5 μm to 150 μm.

In some embodiments, the implant scaffold comprises residual amounts of an organic solvent.

In some embodiments, the polymeric material comprises two biodegradable polymers.

In some embodiments, the implant scaffold is for use in muscle and nerve regeneration.

According to another aspect, the present invention provides an implant scaffold comprising a plurality of aligned channels having a diameter in the range of 50 μm to 400 μm, wherein the channels are separated by a porous wall comprising a polymeric material and having a thickness in the range of 5 μm to 150 μm.

In some embodiments, the implant scaffold has a Young's modulus in the range of 10 Kpa to 5000 Kpa.

In some embodiments, the implant scaffold has a total porosity in the range of 90% to 99%.

In some embodiments, the implant scaffold comprises residual amounts of a water-soluble material. In some embodiments, the implant scaffold comprises residual amounts of butenediol vinyl alcohol (BVOH), polyvinyl alcohol (PVA), or both.

In some embodiments, the polymeric material comprises two biodegradable polymers.

In some embodiments, the implant scaffold is for use in muscle and nerve regeneration.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2B depicts the micro-fiber bridged location in 3D; FIG. 2C represents micro-computed tomography scans of printed BVOH fiber arrays of different lengths. Fibers were of a lateral diameter of 250 μm and vertical diameter of 200 μm. Upper panel presents 2D sections (side view) and lower panel presents 3D reconstructions where the side support regions are sliced away for better visibility of the fibers. Scale bar indicates 1 mm.

FIGS. 3A-3J present SEM micrographs (IX) and μCT imaging (III) of BVOH template (FIG. 3A); μCT imaging of the scaffold of the invention (FIG. 3B); SEM micrographs of the scaffolds showing cross sections (IX) and longitudinal section (III) (FIG. 3C); picture of higher magnification showing pores in walls separating channels (FIG. 3D); a bar graph showing the Young's modulus measurements of the scaffold of the invention (FIG. 3E); graphs of the pore distribution by diameter (FIG. 3F); FIG. 3G represents pore size distribution in 3D reconstructions in salt-leached scaffolds (FIG. 3G-I), in the scaffold (FIG. 3G-II) and an overlap (FIG. 3G-III); FIG. 3H represents porosity measurements; FIG. 3I exhibits average scaffold components representation; FIG. 3J is a bar graph, showing Young's modulus of freeze-dried PLLA/PLGA scaffold of the invention compared to non-porous PLLA/PLGA scaffolds.

FIGS. 4A-4E present pictures of dental pulp stem cells (DPSC) growth (FIG. 4A), engineered blood vessels cultured on scaffold (FIG. 4B), induced pluripotent stem cell derived neurons (iPSC) filling the channels within the scaffold of the invention (FIG. 4C), and scaffold of the invention supporting neurite extension (FIG. 4D-II) compared to fibrin suspension (FIG. 4D-I); FIGS. 4E-I, 4E-II represent midsectioned 3D reconstructions of iodine diffusion into 3D cell cultures on day 3. FIG. 4E-I shows diffusion in a hydrogel plug. FIG. 4E-I shows diffusion in the scaffold of the invention. Yellow staining marks areas where diffusion is effective. FIG. 4F represents micrographs of iPSC-derived cell bodies and axons fascicules inside porous channels and their caudal projections to the host. Green staining is $\beta_{III}$ tubulin staining, cell nuclei indicated by DAPI (blue) staining. Scale bar indicates 200 μm in A and B, 500 μm in C, 50 μm in D and 20 μm in F.

FIG. 6A shows scaffold implantation. Left upper image shows a complete spinal cord transection and right image demonstrates scaffold implantation in the lesion site. Lower image shows the ventral aspect Ex vivo two weeks post lesion and implantation. FIGS. 6B-C show hematoxylin and eosin-stained images of injured spinal cord 4 weeks after injection of fibrin gel (FIG. 6B) or implantation of a fibrin-loaded scaffold of the invention (FIG. 6C). FIG. 6D represents quantification of new tissue area in the lesion between the transected stumps of the spinal cord. FIGS. 6E-F show Immunolabeling of regenerating axons as indicated by anti-$\beta_{III}$ tubulin staining. Images show injured spinal cords injected with fibrin (FIG. 6E) or implanted with scaffolds (FIG. 6F). Dashed lines indicate the borders of the injury. FIGS. 6G-H show high magnification images of Beta-tubulin (green) staining and DAPI staining (blue) inside porous walls of the scaffold (FIG. 6G) or inside guidance channels (FIG. 6H). FIG. 6I represents quantification of tubulin area in porous walls and channels. Scale bars indicate 500 μm in E, and F, 1 mm in B and C and 30 μm in G and H.

FIG. 7A shows regenerating axons in complete spinal cord transection after implantation of fibrin loaded PLLA/PLGA scaffold of the invention. Left image demonstrates cell nuclei indicated by DAPI staining, middle image demonstrates axons indicated by $\beta_{III}$ tubulin staining and right image is a merge of both channels. FIG. 7B shows polar plotting of axonal orientation in scaffolds. FIG. 7C shows regenerating axons in complete spinal cord transection injected with fibrin hydrogel (control). FIG. 7D shows polar plotting of axonal orientation in control group. FIG. 7E is an analysis of axonal orientation in vivo. Scale bar indicates 100 μm.

DETAILED DESCRIPTION OF THE INVENTION

According to some embodiments, the present invention provides a method for making scaffold, comprising providing a 3D template generated according to an image of a target site, contacting the 3D template with a solution comprising a polymeric precursor, thereby filling a space in the 3D template, and evaporating the solution, thereby obtaining a scaffold. In some embodiments, the scaffold is an implant scaffold. In some embodiments, the target site refers to a region of a biological organism. In some embodiments, the target site is a lesion site. In some embodiments, the implant scaffolds are produced by 3D printing. Implant scaffolds according to the present invention can be custom designed to fit a particular subject's anatomy.

In some embodiments, the method further comprises the step of dissolving the 3D template (also referred to as "template").

In some embodiments, the method comprises:
(i) printing a multilayer 3D template according to an image of a target site;
(ii) contacting the 3D template with a solution comprising a polymeric precursor (such as a biodegradable polymer), thereby filling a space in the 3D template; and
(iii) evaporating the solution to obtain the scaffold;
wherein:
the multilayer 3D template comprises a support layer and a geometrical layer;
the multilayer 3D template comprises a releasable polymer;
each layer of the multilayer 3D template comprises a pattern of aligned structures.

In some embodiments, the multilayer 3D template comprises plurality of alternating layers. In some embodiments, the plurality of alternating layers comprises a repeated pattern of the geometrical layer on top of the support layer.

In some embodiments, evaporating the solution comprises lyophilization.

In some embodiments, the image of a lesion site is obtained by a method selected from a magnetic resonance imaging (MM), X-ray image, a computed tomography (CT) scan, positron emission tomography (PET) or any combination thereof.

In some embodiments, the method comprises the step of scanning a region in need of treatment and printing an implant scaffold as described herein.

In some embodiments, providing a 3D template comprises printing. In some embodiments, printing is 3D printing.

Micro-Bridging Pattern Technique

In some embodiments, the method of the invention comprises printing a multilayer 3D template according to an image of a target site. In some embodiments, the 3D template is as described hereinbelow. In some embodiments, the 3D template comprises a pattern. In some embodiments, the 3D template comprises a pattern of aligned geometric forms.

In some embodiments, printing comprises 3D printing. Various 3D printing techniques are known in the art, comprising inter alia extrusion printing, fused deposition modeling, photolithography, stereoliotgraphy (SLA), digital light processing (DLP), and low force stereolitography (LFS). In some embodiments, printing is by a micro-bridging pattern technique.

Figure 1A:
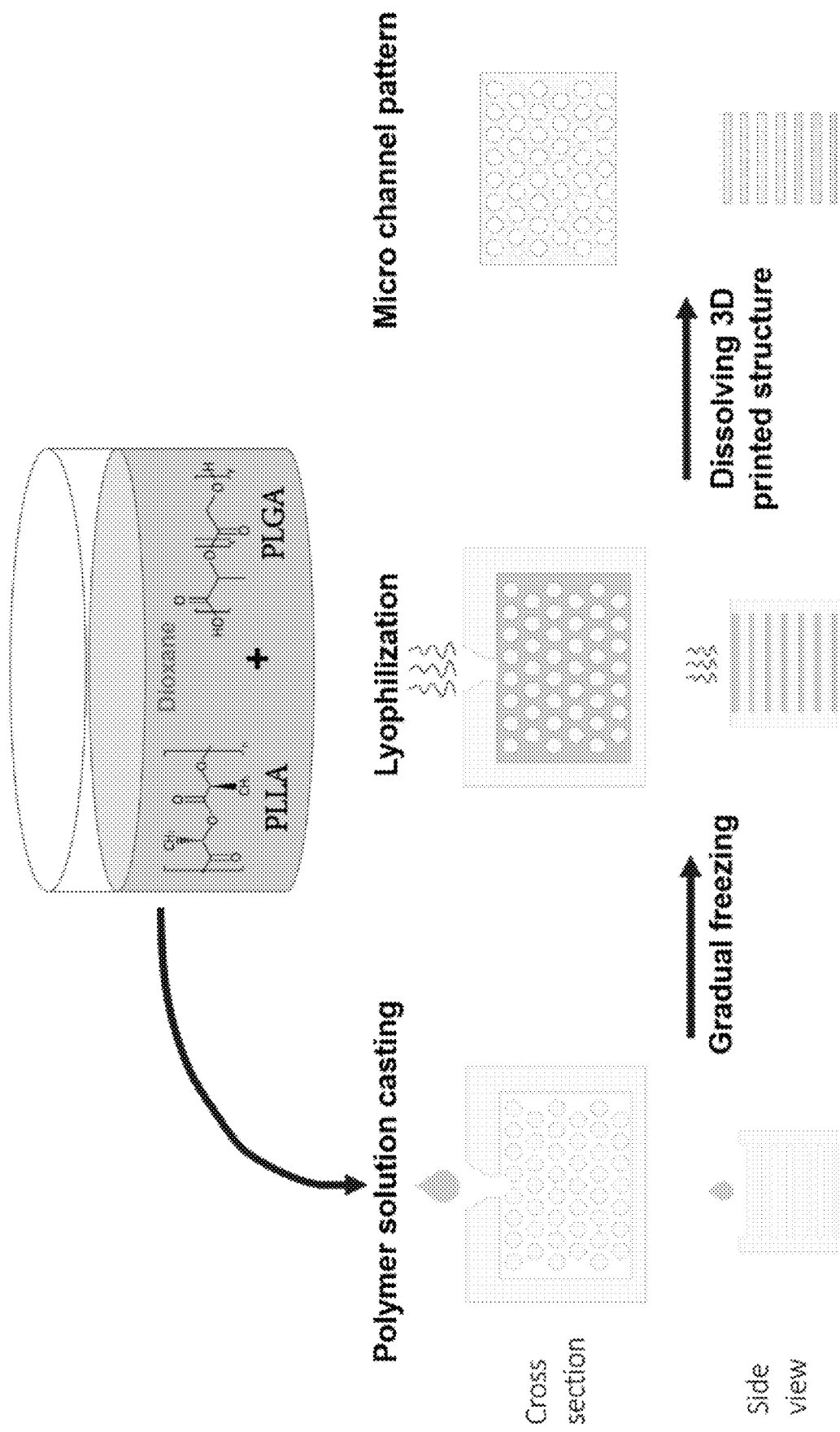
FIGS. 1A-1D present a non-limiting scheme of the fabrication concept and micro patterning of biodegradable scaffolds: 3D printed water-soluble constructs are loaded with polymer solution followed by gradual freezing and lyophilazation of the solvent; The 3D printed construct is then dissolved in water to generate linearly oriented guidance channels (FIG. 1A); description of the printing pattern (FIG. 1B); slicing of 3D printed structures (FIG. 1C and FIG. 1D).
Figure 1D:
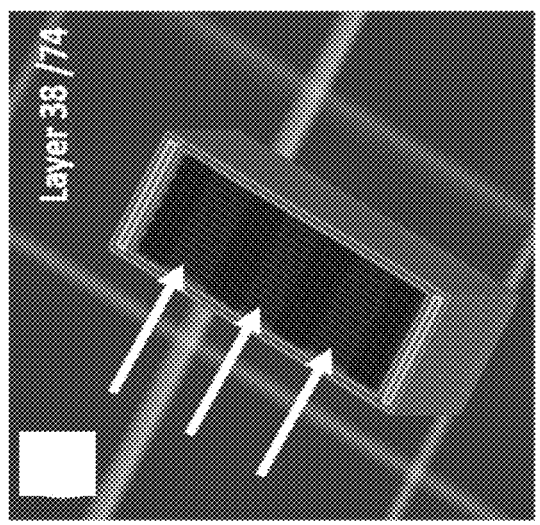
Figure 1C:
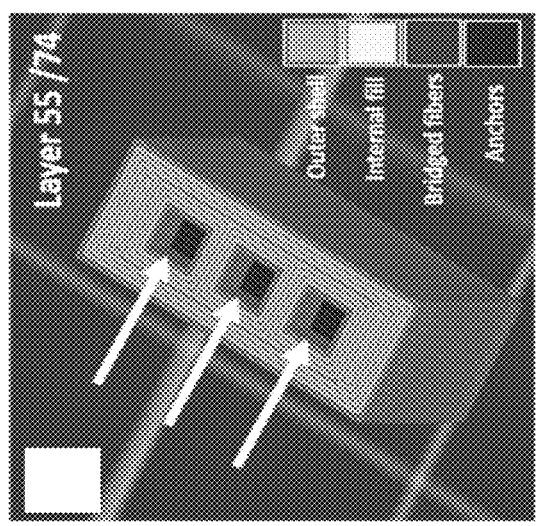
Figure 1B:
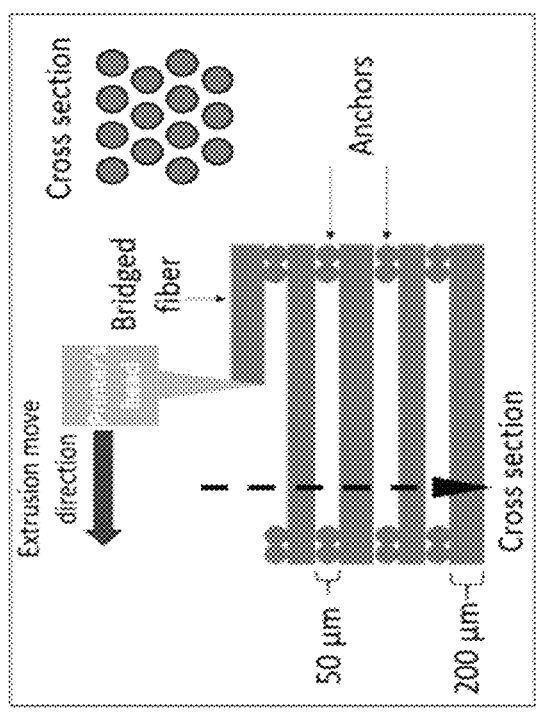

Reference is now made to FIGS. 1B-D, which illustrate an exemplary printing pattern. In some embodiments, the aligned geometric forms are bridged in the air between anchors without support from bellow, to generate a spaced micro-array of aligned geometric forms. In some embodiments, the solution comprising a polymeric precursor is injected in the spaced micro-array.

Reference is now made to FIG. 1C. In some embodiments, the 3D template comprises inlet channels for solution injection. Each inlet channel directs the solution comprising a polymeric precursor into a separate confound cavity which determines the shape and measurements of each scaffold. In some embodiments, the confound cavity is rectangular shaped. In some embodiments, a confound cavity comprises two types of layers. In some embodiments, a confound cavity comprises an anchor layer or a support layer and a geometrical layer (bridged fibers). The anchor layers are only printed on the margins of the cavities and the geometrical layer is printed between every two anchors, as presented in FIG. 1B.

In some embodiments, the method of forming template is by digital 3D printing. In some embodiments the first composition or the second composition is contacted with or is deposited on the substrate by dispensing the molten resin from a dispensing head (also referred to as a "nozzle") of a printing apparatus. In some embodiments, dispensing comprises a predetermined amount (e.g. volume) of the resin. In some embodiments, the nozzle of a printing apparatus is movable in a controlled manner along X and Y axes, so as to enable printing a predetermined pattern on the substrate. In some embodiments, the predetermined pattern is according to an image of the target site, as described herein. In some embodiments, the predetermined pattern is a three-dimensional (3D) pattern of the target site. In some embodiments, the predetermined pattern comprises a dimension of a target site (e.g. lesion) as obtained from the image. In some embodiments, a shape of the 3D template is according to 3D shape of the target site. In some embodiments, a dimension of the 3D template is according to a dimension of the target site, wherein the target site is as described herein. In some embodiments, a dimension or shape of the 3D template is according to a dimension or shape of the target site as provided by an image of the target site. In some embodiments, a dimension or shape of an exterior wall of the 3D template is according to a dimension or shape (e.g. interior dimension or shape) of the lesion site as provided by an image of the lesion site. In some embodiments, the nozzle of a printing apparatus is movable in a controlled manner along X, Y and Z axes, so as to enable printing a predetermined three-dimensional (3D) object on the substrate (e.g. a printing support, as described below).

In some embodiments, the movement of the nozzle is under the control of a computer-controlled, CAD/CAM system in which the design of the pattern or of the 3D object to be formed is initially created on a computer. In some embodiments, a software is utilized to translate the 3D image data in the computer into a controlled movement of the nozzle through a predetermined pattern of movement to successively deposit a layer of material according to the desired pattern or shape.

As used herein, the term "micro-bridging" refers to a process where the geometrical layers are extruded in the air without support from below to generate a spaced micro-array of aligned geometric forms. Micro-bridging may be achieved due to the high solidification rate of thermoplastic materials and with the assistance of a cooling fan in the printer.

Figure 2A:
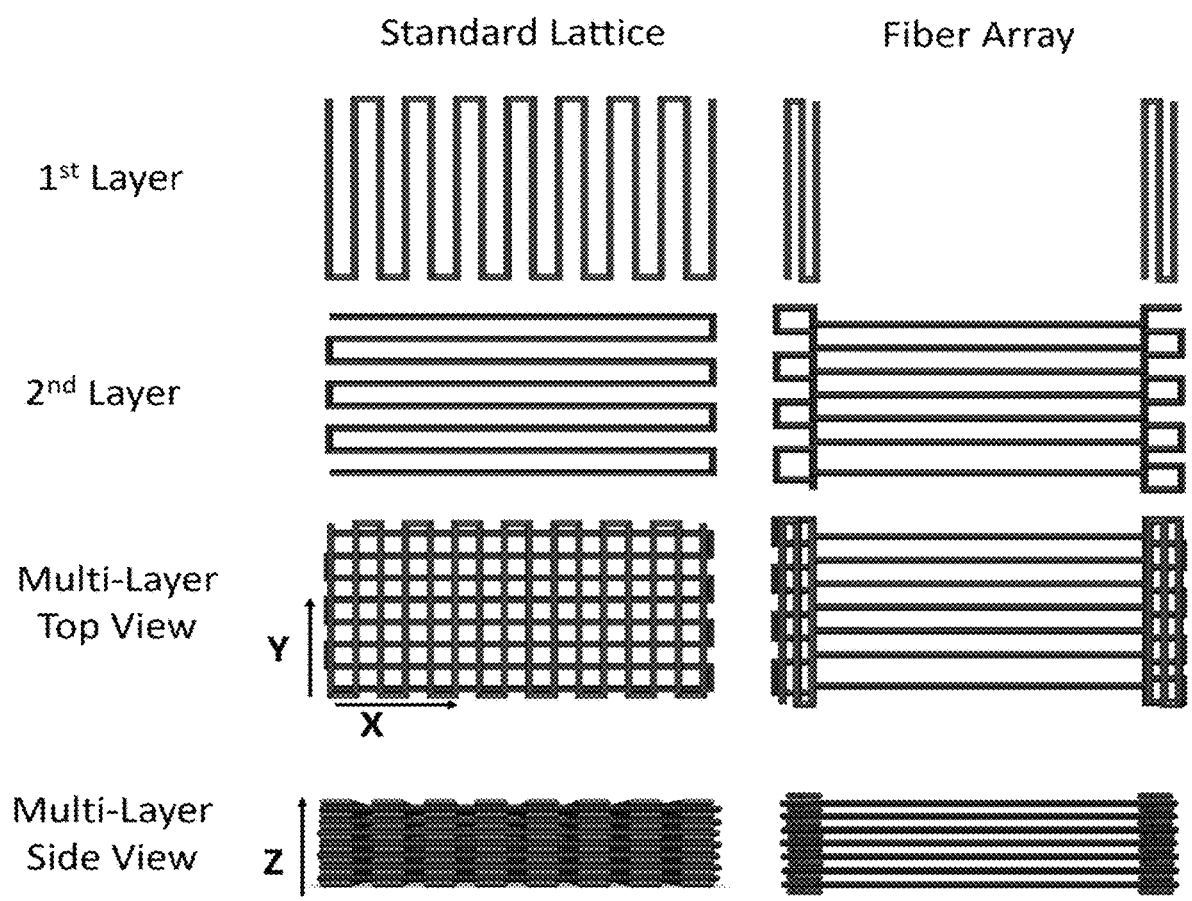
FIGS. 2A-2C present a non-limited schematic representation of a standard rectilinear printing pattern wherein all spaces between fibers are interconnected as opposed to the micro-bridging technique described herein, wherein the space where the polymer solution is casted into (scaffold area) is separated from the rest of the template and aligned arrays of micro-fibers are formed within this space (FIG. 2A).

In some embodiments, micro-bridging is for forming the template comprising a plurality of printed layers. In some embodiments, each of the plurality of layers comprises a plurality of arrays comprising the resin. In some embodiments, the plurality of arrays is bridging between two bottom anchors, wherein the anchors are positioned within a horizontal plane. In some embodiments, the plurality of arrays is bridging between two support layers positioned within a horizontal plane (FIGS. 2A and 2C).

In some embodiments, micro-bridging comprises extruding a filament of a molten resin and simultaneously drying the extruded filament. In some embodiments, the resin comprises a releasable polymer, as described hereinbelow.

The term "resin", as described herein is referred to a composition or a material applicable for 3D printing process, i.e. it can be melted under conditions of the 3D printing process, and it can be subsequently dried or cured to provide a printed 3D article or object. Drying is as described herein. Curing can be carried out in any manner, such as for instance, irradiating with electromagnetic radiation having sufficient energy to initiate a polymerization or cross-linking reaction. In some embodiments, the resin comprises a monomeric chemical species, such as a chemical species having one or more functional groups or moieties that can react with the same or different functional groups or moieties of another monomeric chemical species to form one or more covalent bonds, such as in a polymerization reaction. In some embodiments, the resin comprises a releasable polymer being compatible with 3D printing process (e.g. extrusion process). In some embodiments, the resin comprises an extrudable polymer. As used herein the term "extrudable polymer" refers to a polymer having improved physical properties such as melt viscosity, temperature stability, and tensile strength sufficient for use in extrusion-based 3D printing process. In some embodiments, the resin comprises a polyalcohol. In some embodiments, the resin comprises a poly ether or a polyvinyl alcohol, including a mixture or a copolymer thereof. In some embodiments, the resin comprises butenediol-co-vinyl alcohol (BVOH).

In some embodiments, the resin comprises a releasable polymer, as described hereinbelow. Optionally, the "resin" refers to a composition comprising at least one of: a monomer, an oligomer, a polymer or a mixture thereof.

In some embodiments, drying comprises solidifying of a resin in a molten state. In some embodiments, drying comprises exposing the molten resin to electromagnetic radiation (such as thermal radiation, UV-radiation, electron beam, X-ray) for a time sufficient for at least partial solidification of the resin. In some embodiments, drying comprises a process selected from thermal curing and UV-curing. In some embodiments, drying comprises thermal curing and UV-curing.

In some embodiments, drying and printing are performed simultaneously or subsequently. In some embodiments, drying is by any of: cold drying, convection drying, infrared (IR) drying, microwave drying and vacuum drying. In some embodiments, drying is by curing, such as UV-curing. In some embodiments, drying is by convection drying, such as by applying a gas stream to the extruded filament.

In some embodiments, cold drying comprises applying a gas stream to the extruded filament, wherein the gas stream is at a temperature between 0 and 60° C., between 0 and 10° C., between 10 and 20° C., between 20 and 30° C., between 30 and 50° C., between 50 and 80° C., between 80 and 100° C. including any range therebetween. In some embodiments, the gas stream comprises de-humidified gas. In some embodiments, cold drying and printing are performed simultaneously or subsequently during the micro-bridge printing process. In some embodiments, cold drying is applied within a time period between 0.1 and 100 s (seconds), between 0.1 and 1 s, between 1 and 5 s, between 5 and 10 s, between 10 and 20 s, between 20 and 60 s, between 60 and 100 s, including any range therebetween, wherein the time period is from printing onset of each 3D-printed array (fiber).

In some embodiments, drying comprises a partial drying of the composition. In some embodiments, drying is by solidifying of at least 30%, at least 50%, at least 60%, at least 70%, at least 80%, at least 90%, at least 95%, at least 97% per weight of the resin. In some embodiments, drying is by exposing the resin to a cold drying. In some embodiments, drying is by exposing the resin to electromagnetic radiation in a visible and/or infrared-light spectrum.

Generally, the drying method and exact drying conditions selected will depend upon, among other things, chemical and physical properties of materials composing the resin, and dimension of the resulting printed layer.

In some embodiments, drying comprises exposing the molten resin to a gas stream under conditions suitable for drying or solidifying of at least a part of the molten resin.

In some embodiments, conditions suitable for drying comprise exposure to a gas stream for a time ranging from 0.1 to 100 s (seconds). In some embodiments, conditions suitable for drying are adjusted so as to result in a stable layer comprising a plurality of patterned arrays. In some embodiments, conditions suitable for drying are adjusted so as to result in a stable layer of cylindrical arrays, wherein at least a part of the arrays are devoid of contact with any of the bottom layer and the subsequent layer. As used herein, the term "stable" refers to the capability of the layer or of the template to maintain its structural and/or mechanical integrity. In some embodiments, the template is referred to as stable, if the template is characterized by a mechanical integrity sufficient to provide a support for a polymeric precursor so as to form a polymeric scaffold having a predetermined geometry and/or dimension.

In some embodiments, conditions suitable for drying comprise drying time ranging from 0.1 to 100 s, from 0.1 to 100 s, from 0.1 to 100 s, from 0.1 to 100 s, from 0.1 to 100 s, from 0.1 to 100 s, from 0.1 to 100 s, from 0.1 to 100 s, from 0.1 to 100 s, from 0.1 to 100 s, from 0.1 to 100 s, including any range or value therebetween.

In some embodiments, printing (e.g. by extruding the molten resin) and drying are performed simultaneously, so as to obtain a solidified printed layer. In some embodiments, printing speed is adjusted so as to allow solidifying of at least 50%, at least 60%, at least 70%, at least 80%, at least 90%, at least 95%, at least 97%, of the molten resin.

Exemplary micro-bridging conditions are provided in the Examples section below.

In some embodiments, the method of providing or forming the template comprises providing a substrate and printing a first bottom layer in contact with the substrate. In some embodiments, printing is as described hereinabove. In some embodiments, the substrate is a solid substrate comprising any one of: a polymeric substrate, a glass substrate, and a metallic substrate, or any combination thereof. In some embodiments, the substrate comprises a printing platform. In some embodiments, a substrate comprises a printing platform. In some embodiments, the substrate has an adhesiveness property to a substrate, wherein adhesiveness is described hereinbelow.

In some embodiments, the substrate is further in contact with an adhesive layer, so as to provide adhesiveness to the bottom layer. In some embodiments, the outer surface of the substrate is capable of binding the resin. In some embodiments, the outer surface of the substrate is capable of binding a resin in a molten state. In some embodiments, the outer surface of the substrate is capable of binding a resin, wherein the resin is at a temperature above its melting point (Tm). In some embodiments, binding and/or adhesiveness is by forming a covalent bond, a non-covalent bond, or both.

In some embodiments, the bottom layer is at least partially in contact with the substrate. In some embodiments, the bottom layer is a continuous layer. In some embodiments, the bottom layer comprises a plurality of aligned arrays. In some embodiments, each of the plurality of aligned arrays is in contact with an adjacent array. In some embodiments, the bottom layer is printed by extrusion printing.

In some embodiments, the method of providing or forming the template comprises a step of printing an additional layer on top of the bottom layer. In some embodiments, printing is as described hereinabove. In some embodiments, the additional layer is a support layer (also referred to as an anchor layer).

In some embodiments, the method comprises subsequent printing of the plurality of layers by micro-bridging. In some embodiments, the method comprises printing the support layer and subsequently printing the geometrical layer. In some embodiments, printing any of the support layer or the geometrical layer comprises generating a plurality of geometrical forms by micro-bridging. In some embodiments, the method comprises printing a plurality of distant geometrical forms. In some embodiments, the method comprises printing a plurality of horizontally aligned geometrical forms. In some embodiments, the method comprises printing a plurality of horizontally aligned parallel cylinders. In some embodiments, the parallel cylinders are aligned according to pattern, as described hereinbelow. In some embodiments, printing any of the support layer or the geometrical layer comprises patterning alternating layers of parallel aligned cylinders. In some embodiments, patterning is according to an image of the target site, as described herein.

In some embodiments, printing the support layer comprises printing a plurality of parallel cylinders aligned along a transversal axis of the 3D template. In some embodiments, printing the geometrical layer comprises printing a plurality of parallel cylinders aligned along a longitudinal axis of the 3D template. In some embodiments, the plurality of parallel cylinders are as described hereinbelow. In some embodiments, the 3D template is printed according to an image, as described hereinabove.

In some embodiments, the micro-bridging process is repeated layer by layer to generate a spaced array of linear geometrical forms within the entire cavity (3D template). To ensure that the cavity of the scaffold is confound in each layer, the bridged geometrical layers (bridged fibers) are shifted by 90 degrees (or according to the angle of the anchor layer) every time they reach the anchor from bellow.

According to the present invention, the size, spacing and shape of the linear geometrical forms can be chosen to obtain custom-made implant scaffolds. In some embodiments, the method comprises alternating printing of the support layer and of the geometrical layer, thereby generating the 3D template. In some embodiments, printing steps are repeated from 1 to 1000, from 1 to 10, from 10 to 20, from 20 to 30, from 30 to 40, from 40 to 50, from 50 to 100, from 100 to 200, from 200 to 300, from 300 to 500, from 500 to 1000 times including any range or value therebetween. In some embodiments, number of repeats predetermines the height or thickness of the 3D template. In some embodiments, a template dimension and/or geometrical form (e.g. shape) predetermines a dimension and/or geometrical form of the scaffold.

In some embodiments, the method comprises a step of contacting the 3D template with a solution comprising a polymeric precursor. In some embodiments, the method comprises a step of mixing a polymeric precursor with a solvent to obtain a solution, and subsequently contacting the solution with the 3D template. In some embodiments, mixing optionally comprises providing the mixture to a temperature suitable for dissolution of the precursor. In some embodiments, the polymeric precursor comprises a plurality of polymers. In some embodiments, the plurality of polymers are mixed simultaneously with the solvent. In some embodiments, mixing comprises mixing the first polymer with the solvent to obtain a first mixture, mixing the second polymer with the solvent to obtain a second mixture, and subsequently combining the first mixture and the second mixture so as to obtain the solution.

In some embodiments, the polymeric precursor comprises a biodegradable polymer. In some embodiments, the polymeric precursor remains stable upon removing or releasing the template, wherein stable is as described herein. In some embodiments, the polymeric precursor is physically and/or chemically inert to the removing conditions of the template. In some embodiments, the polymeric precursor is as described herein.

In some embodiments, the solvent is any solvent compatible with the 3D template. In some embodiments, the 3D template remains stable upon contacting with the solvent, wherein stable is as described hereinabove. In some embodiments, the 3D template maintains substantially its integrity upon contacting with the solvent, wherein substantially is as described hereinbelow. In some embodiments, the 3D template is substantially non-dissolvable or non-dispersible in the solution. In some embodiments, the 3D template is substantially non-dissolvable or non-dispersible in the solution at a temperature between 10 to 80° C., between 10 and 20° C., between 20 and 25° C., between 25 and 30° C., between 30 and 35° C., between 35 and 40° C., between 40 and 45° C., between 45 and 50° C., between 50 and 55° C., between 55 and 60° C., between 60 and 80° C., including any range or value therebetween. In some embodiments, the 3D template is physically and/or chemically inert to the solvent. In some embodiments, substantially comprises at least 60%, at least 70%, at least 80%, at least 85%, at least 90%, at least 95%, at least 92%, at least 97% of the total weight including any range or value therebetween.

In some embodiments, the concentration of the polymeric precursor within the solution is so as to result in a scaffold having sufficient mechanical properties (e.g., Young's modulus). In some embodiments, the mechanical properties of the scaffold are predetermined by the concentration of the polymeric precursor within the solution. In some embodiments, the concentration of the polymeric precursor predetermines porosity of the scaffold, wherein the porosity relates to a porosity of the plurality of walls, as described herein. In some embodiments, the mechanical properties of the scaffold are predetermined by mechanical properties of the target site.

In some embodiments, the concentration of the polymeric precursor (e.g. a mixture of PLLA and PLGA) in the solution is 1% to 50% (w/v %). In some embodiments, the concentration of the polymeric precursor in the solution is 1% to 45% (w/v %), 1% to 10% (w/v %), 1% to 5% (w/v %), 5% to 10% (w/v %), 10% to 40% (w/v %), 10% to 20% (w/v %), 20% to 30% (w/v %), 30% to 40% (w/v %), 40% to 50% (w/v %), 5% to 20% (w/v %), 5% to 30% (w/v %), or 10% to 40% (w/v %), including any range therebetween.

In some embodiments, the polymeric precursor is substantially soluble or dispersible within the solvent. In some embodiments, the polymeric precursor is substantially soluble within the solvent at a temperature between 10 to 80° C., between 10 and 20° C., between 20 and 25° C., between 25 and 30° C., between 30 and 35° C., between 35 and 40° C., between 40 and 45° C., between 45 and 50° C., between 50 and 55° C., between 55 and 60° C., between 50 and 80° C., between 50 and 75° C., between 50 and 70° C., between 60 and 75° C., between 60 and 70° C., between 65 and 75° C., between 65 and 80° C., including any range or value therebetween. In some embodiments, the polymeric precursor has a solubility within the solvent of at least 10 g/L, at least 20 g/L, at least 30 g/L, at least 40 g/L, at least 50 g/L, at least 60 g/L, at least 70 g/L, at least 80 g/L, at least 100 g/L, including any range or value therebetween.

In some embodiments, the polymeric precursor comprises a polymer, a monomer or both. In some embodiments, the polymeric precursor comprises a monomer capable of polymerization so as to form a polymeric chain. In some embodiments, the polymeric chain is at least partially biodegradable or biocompatible, as described herein. Such polymerizable monomers are well-known in the art and may include inter alia lactide, caprolactone, ethylene glycol, etc. In some embodiments, the polymeric precursor comprises a cross-linkable polymer and a cross-linking agent (such cross-linkable polymers and cross-linking agents are well-known in the art). In some embodiments, the polymeric precursor comprises a polymer or a mixture of polymers. In some embodiments, the polymeric precursor is at least partially biodegradable or biocompatible. In some embodiments, the polymeric precursor is as described hereinbelow.

In some embodiments, the solvent is an organic solvent. In some embodiments, the solvent is a hydrophobic solvent. In some embodiments, the solvent is a water miscible or a water immiscible solvent. In some embodiments, the solvent is compatible with a lyophilization step, as described below. Non-limiting examples of solvents include but are not limited to dioxane, dimethylsulfoxide, tetrahydrofuran, acetonitrile, chloroform, dichloromethane, tert-butanol, propanol, pentanol, acetone, isopropanol, ethyl acetate, methylethyl ketone, methyl-tetrahydrofuran, pyridine, or any combination thereof. In some embodiments, the solution comprises dioxane as a solvent.

In some embodiments, contacting is by injecting, dipping, submerging, and spraying or a combination thereof. In some embodiments, contacting is by injecting a solution via an opening in the template as exemplified by FIG. 1A. In some embodiments, the solution comprising a polymeric precursor is contacted with at least a part of the plurality of the aligned geometric forms (e.g. aligned cylinders).

In some embodiments, the 3D template comprises an exterior wall. In some embodiments, the exterior wall of the 3D template defines a chamber. In some embodiments, the exterior wall of the 3D template forms a chamber, wherein the wall comprises at least one opening. In some embodiments, contacting the 3D template with the solution is via an opening. In some embodiments, contacting the 3D template with the solution comprises providing (e.g. by injecting) the solution via the opening. In some embodiments, contacting the 3D template with the solution comprises providing (e.g. by injecting) the solution via the opening, thereby contacting the interior of the 3D template with the solution. In some embodiments, the interior of the 3D template refers to a lumen defined by at least a wall of the 3D template. In some embodiments, the 3D template is placed within a container and subsequently contacted with the solution.

In some embodiments, contacting the 3D template with a solution comprising a polymeric precursor is for filling a space within the 3D template. In some embodiments, the space is formed by distant cylinders within any of the support layer and of the geometrical layer. In some embodiments, the space is formed by subsequent layers, such as by adjacent support layer and the geometrical layer. In some embodiments, at least 50%, at least 60%, at least 70%, at least 80%, at least 90%, at least 95%, at least 97%, of the open space within the 3D template is filled by the solution comprising a polymeric precursor.

In some embodiments, contacting is for a time sufficient for filling the open space or lumen within the 3D template. In some embodiments, contacting is for a time sufficient for the solution to percolate within the entire cavity of the 3D template.

In some embodiments, contacting further comprising applying mechanical force (e.g. vibration, shaking, centrifugation, ultra-sonication) so as to improve percolation of the solution within the entire cavity of the 3D template.

In some embodiments, the method comprises evaporating the solvent form the solution in contact with the template. In some embodiments, evaporating is for obtaining a scaffold characterized by a plurality of porous walls, wherein the walls are as described herein.

In some embodiments, evaporating is by applying vacuum. In some embodiments, evaporating is by exposing the template to a temperature of more than 25° C. and to a reduced pressure (vacuum). In some embodiments, evaporating is by lyophilization (freeze drying).

As used herein, the term "lyophilization" or "freeze-drying" or "vacuum drying" refers to the known process of freezing of a liquid product, whereupon the frozen product is dried by sublimation.

In some embodiments, the method further comprises removing or releasing the template. In some embodiments, the method further comprises removing or releasing at least a part of the releasable polymer of the template. In some embodiments, the method comprises removing at least 50%, at least 60%, at least 70%, at least 80%, at least 90%, at least 95%, at least 97% by weight of the releasable polymer.

In some embodiments, removing or releasing is by applying to the releasable polymer or to the template any of an organic solvent, a polar solvent, thermal energy, a reagent (e.g. a nucleophile, an oxidizing agent, a reducing agent, an acid or a base), ultrasound or a combination thereof. In some embodiments, applying under conditions (e.g. time, and temperature) sufficient for at least partial dissolution of the releasable polymer or the template.

In some embodiments, the releasable polymer is removed by dissolving. In some embodiments, dissolving is by contacting the releasable polymer or the template with a solvent capable of at least partially dissolving the releasable polymer, wherein partially is as described hereinabove. In some embodiments, removing is by contacting the releasable polymer (e.g. BVOH) or the template with an aqueous solution under conditions sufficient for at least partial dissolution of the releasable polymer or the template, wherein partial is as described hereinabove. In some embodiments, conditions sufficient for dissolution comprising temperature between 10 to 80° C., between 10 and 20° C., between 20 and 25° C., between 25 and 30° C., between 30 and 35° C., between 35 and 40° C., between 40 and 45° C., between 45 and 50° C., between 50 and 55° C., between 55 and 60° C., between 50 and 80° C., between 50 and 75° C., between 50 and 70° C., between 60 and 75° C., between 60 and 70° C., between 65 and 75° C., between 65 and 80° C., including any range or value therebetween. In some embodiments, conditions sufficient for dissolution comprising contacting time between 1 minutes (min) and 48 hours (h), between 1 min and 1 h, between 1 h and 5 h, between 5 h and 10 h, between 10 h and 15h, between 15 h and 24 h, between 24 h and 30 h, between 30 h and 40 h, between 40 h and 48 h, between 48 h and 72 h, including any range or value therebetween.

In some embodiments, the method comprises at least partial removal the water-soluble template (e.g. BVOH-based template) by dissolving the template in an aqueous solution, thereby obtaining the scaffold of the invention. In some embodiments, the scaffold is an implant scaffold comprising a plurality of open channels or lumens as described hereinbelow. Exemplary removing conditions are described in greater detail in the Examples section.

Template

In another aspect, provided herein is a 3D template. In some embodiments, the template comprises a plurality of layers. In some embodiments, the template comprises a plurality of alternating layers. In some embodiments, the plurality of alternating layers comprises a repeated pattern of the geometrical layer and of the support layer.

In some embodiments, the 3D template is manufactured by 3D printing. In some embodiments, the 3D template is manufactured according to the method of the invention as described hereinabove. In some embodiments, the 3D template is printed according to an image of the target site (e.g. a lesion site). In some embodiments, a dimension of the 3D template is according to a dimension of the lesion site as obtained from the image, wherein the image is as described hereinabove. In some embodiments, the dimension as used herein is referred to a geometrical form or shape of the template.

In some embodiments, the 3D template is solid at a temperature between 0 to 50° C., between 10 to 30° C., between 20 to 30° C., between 10 and 20° C., between 30 and 50° C., between 25 to 40° C., including any range therebetween.

In some embodiments, the template is solid at a temperature of less than 180° C., less than 150° C., less than 120° C., less than 100° C., less than 80° C., less than 60° C., including any range or value therebetween.

The template as described herein, in some embodiments, can have a melting point or a freezing point compatible with the operable temperature of scaffold manufacturing process.

In some embodiments, the 3D template provides a support for the scaffold. In some embodiments, the 3D template provides a support for the solution comprising the polymeric precursor. In some embodiments, the 3D template predetermines the shape and structure of the scaffold.

In some embodiments, the 3D template is sufficiently stable, i.e. is characterized by a mechanical integrity sufficient to provide a support for scaffold formation. In some embodiments, the stable template is configured to provide a support for the scaffold. In some embodiments, the template is referred to as stable, if the template substantially maintains its structural and/or mechanical integrity under conditions of a scaffold manufacturing process. In some embodiments, the stable composition is chemically inert to the conditions of a scaffold manufacturing process. The conditions of scaffold manufacturing process may comprise parameters such as operable temperature, exposure to a solvent, mechanical stress (e.g., vibration, centrifugal forces, and ultra-sonic waves, etc.). In some embodiments, the stable template is rigid under scaffold manufacturing conditions.

In some embodiments, the template is a printed 3D template comprising any material which can be removed or released (e.g. by solubilization) without disturbing the porosity and the structural intactness of the final scaffold. In some embodiments, the 3D template comprises any material which can be removed or released without significantly altering the porosity and structural intactness (such as shape) of the final implant scaffold. As used herein, without significantly altering refers to altering not more than 0.01%, 0.1%, 0.5%, 1%, 2%, 5% or 10%, of the porosity and structural intactness (such as shape) of the final implant scaffold.

In some embodiments, the 3D template comprises a polymeric material. In some embodiments, the 3D template comprises a 3D-printable material or a 3D-printable polymer, as described herein. In some embodiments, the 3D template comprises a solidified resin, wherein the resin is as described herein.

In some embodiments, the 3D template comprises a releasable polymer. In some embodiments, the releasable polymer is biodegradable, biocompatible or both. In some embodiments, the releasable polymer comprises any polymer which is at least partially removed or released by applying any of an organic solvent, a polar solvent, an aqueous solution, thermal energy, a reagent (e.g. a nucleophile, an oxidizing agent, a reducing agent, an acid or a base), ultrasound or a combination thereof. In some embodiments, at least partially removed or released is as described herein. In some embodiments, the releasable polymer is removed or released under conditions (e.g. time, and temperature) sufficient for at least partial removal of the releasable polymer.

In some embodiments, the releasable polymer comprises a dissolvable polymer. In some embodiments, the dissolvable polymer is released or removed by applying a solvent comprising any of an organic solvent, a polar solvent, or an aqueous solution. In some embodiments, applying comprises contacting the dissolvable polymer with the solvent under conditions sufficient for at least partial removal of the dissolvable polymer, as described herein. In some embodiments, the releasable polymer comprises a water-soluble polymer, wherein the water-soluble polymer is substantially dissolvable by an aqueous solution.

In some embodiments, the 3D template comprises a water-soluble polymer or a water-dispersible polymer. Non-limiting examples of water-soluble materials include but are not limited to polymers such as butenediol vinyl alcohol (BVOH), poly (2ethyl-2-oxazoline), polyacrylic acid, carboxymethyl cellulose (CMC), polyvinyl alcohol (PVA), alginate, gelatin, hyaluronic acid, chitosan, and cellulose or water-soluble derivatives thereof; and other materials such as sucrose, lactose, sophorose, or water-soluble derivatives thereof, including any combination and/or copolymers thereof.

In some embodiments, the 3D template comprises BVOH. In some embodiments, at least 70%, at least 80%, at least 90%, at least 92%, at least 95%, at least 97%, at least 99% by weight of the 3D template is BVOH.

In some embodiments, the 3D template is multilayer template comprising alternating support layers and geometrical layers, wherein each layer comprises the releasable polymer. In some embodiments, each layer of the template comprises the water-soluble polymer (e.g. BVOH).

In some embodiments, each layer of the multilayer template comprises a plurality of geometrical forms. In some embodiments, the plurality of geometrical forms is horizontally aligned. In some embodiments, the plurality of geometrical forms have the same shape or geometrical form. In some embodiments, the plurality of geometrical forms have a different shape or geometrical form. In some embodiments, the plurality of geometrical forms has a round or a spherical shape. In some embodiments, at least a part of the plurality of geometrical forms is cylindrically shaped. In some embodiments, at least a part of the plurality of geometrical forms is elliptically shaped. In some embodiments, at least a part of the plurality of geometrical forms as a geometry selected from cylindrical, spherical, round, elliptical, conical or a combination thereof.

In some embodiments, the plurality of geometrical forms is characterized by a pattern. In some embodiments, the pattern is a pattern of aligned structures. In some embodiments, the geometrical forms (e.g. being in a form of aligned structures) comprise the releasable polymer (e.g. BVOH). In some embodiments, aligned structures are in a form of aligned arrays.

In some embodiments, the chamber comprises a minor axis and a major axis. In some embodiments, the template comprises a longitudinal axis and a transverse axis. In some embodiments, the plurality of arrays are aligned along a longitudinal axis, along transversal axis or both.

In some embodiments, the plurality of aligned arrays comprise distant arrays, wherein the distance between adjacent arrays is as described hereinbelow. In some embodiments, the plurality of aligned arrays have the same or different shape or geometrical form. In some embodiments, the shape or geometrical of the plurality of aligned arrays in any one of the layers is the same or different.

In some embodiments, the plurality of aligned arrays are in a form of rods. In some embodiments, the rods comprise any geometrical form (such as cylinder, cuboid, etc.). In some embodiments, the plurality of aligned arrays has a cylindrical form. In some embodiments, the plurality of aligned arrays has a cylindrical form. In some embodiments, the plurality of aligned arrays is in a form of aligned distant cylinders. In some embodiments, each of the aligned cylinders comprises the releasable polymer (e.g. BVOH). In some embodiments, each of the aligned cylinders is a 3D-printed cylinder, wherein printing is as described hereinabove.

A non-limiting configuration of an exemplary template is represented by FIG. 2C.

In some embodiments, the template comprises a plurality of alternating layers. In some embodiments, the template comprises a plurality of geometrical layers and a plurality of support layers. In some embodiments, each layer is a 3D layer.

In some embodiments, the geometrical layer comprises a plurality of distant arrays aligned along the longitudinal axis, wherein the longitudinal axis defines the length of the template (FIG. 2C). In some embodiments, the plurality of distant arrays comprise a plurality of parallel arrays. In some embodiments, the plurality of distant arrays comprise a plurality of parallel cylinders aligned along the longitudinal axis, thus forming the geometrical layer. In some embodiments, the plurality of distant arrays is in a form of cylindrically shaped fibers as exemplified by FIG. 2C. In some embodiments, the geometrical layer is substantially continuous, i.e. the plurality of distant arrays fill at least 60%, at least 70%, at least 80%, at least 90% of volume defined by the geometrical layer. In some embodiments, the volume defined by the geometrical layer is calculated according to an area of the template (as defined by the length and the width of the geometrical layer) multiplied by a height of the geometrical layer, wherein the height is defined as an average diameter of the plurality of cylinders within the geometrical layer.

In some embodiments, the support layer comprises a plurality of distant arrays aligned along the transversal axis, wherein the transversal axis defines the width of the template (FIG. 2C). In some embodiments, the plurality of distant arrays comprise a plurality of parallel arrays. In some embodiments, the plurality of distant arrays comprise a plurality of parallel cylindrically shaped fibers aligned along the transversal axis, thus forming the support layer, as exemplified by FIG. 2C. In some embodiments, the plurality of distant arrays fill at most 50%, at most 40%, at most 30%, at most 20%, at most 10% of volume defined by the support layer. In some embodiments, the volume defined by the support layer is calculated according to area of the template (as defined by the length and the width of the geometrical layer) multiplied by a height of the support layer, wherein the height is defined as an average diameter of the plurality of cylinders within the support layer.

In some embodiments, the plurality of alternating layers is aligned vertically along a Z-axis of the template (FIG. 2C). In some embodiments, the alternating layers are parallel to each other. In some embodiments, each layer defines a surface. In some embodiments, the surfaces are substantially parallel to each other. In some embodiments, the plurality of arrays or cylinders within the entire template form a chess-board pattern.

In some embodiments, the plurality of vertically aligned alternating layers define the height of the template. In some embodiments, the template comprises at least 5, at least 10, at least 15, at least 20, at least 30, at least 40, at least 50, at least 60, at least 70, at least 100 layers including any range or value therebetween. In some embodiments, the number of layers is predetermined by a dimension of the target site, wherein the target site is as described herein.

In some embodiments, the template comprises a plurality of vertically aligned regions, wherein each region comprises the geometrical layer in contact with the support layer. In some embodiments, the length of the template is defined by a number of adjacent regions, wherein each region is defined by an average length of the plurality of arrays within the geometrical layer. In some embodiments, the plurality of geometrical layers within the vertical plane of the template is bridged between the supporting layers.

In some embodiments, the plurality of alternating layers are partially in contact with each other. In some embodiments, the support layer is in contact with the geometrical layer. In some embodiments, the geometrical layer is partially in contact with the support layer. In some embodiments, in contact comprises bound or adhered.

In some embodiments, each pair of subsequent geometrical layers is separated by the support layer. In some embodiments, each pair of subsequent support layers is separated by the geometrical layer.

In some embodiments, a distance between the subsequent geometrical layers is predetermined by the thickness or the height of the support layer, wherein the height of the support layer is as described herein. In some embodiments, a distance between the subsequent geometrical layers is substantially the same along the geometrical layer. In some embodiments, a distance between the subsequent geometrical layers has a standard deviation from 0.1 to 10%, from 0.1 to 1%, from 1 to 5%, from 5 to 10% including any range or value therebetween.

In some embodiments, a distance between the subsequent support layers is predetermined by the thickness or the height of the geometrical layer, wherein the height of the geometrical layer is as described herein.

In some embodiments, at most 50%, at most 40%, at most 30%, at most 20%, at most 10% of an outer surface of the geometrical layer is in contact with the support layer. In some embodiments, at most 50%, at most 40%, at most 30%, at most 20%, at most 10% of the length of the geometrical layer is in contact with or facing the plurality of fibers within the support layer, wherein the length is an average length of the plurality of fibers within the geometrical layer.

In some embodiments, the fiber within the geometrical layer comprises a first end and a second end. In some embodiments, the first end and the second end are aligned along the longitudinal axis of the template. In some embodiments, the distal (or opposing) ends define a length of the fiber. In some embodiments, the ends of the plurality of fibers within the geometrical layer are in contact with the support layer. In some embodiments, the ends of the plurality of fibers within the geometrical layer are in contact with a bottom support layer and with a subsequent support layer.

In some embodiments, each of the distal (or opposing) ends of the geometrical layer is in contact with a support layer. In some embodiments, each of the distal (or opposing) ends of the geometrical layer is in contact with a plurality of support layers. In some embodiments, each of the distal (or opposing) ends of the geometrical layer is in contact with a preceding (or bottom) support layer and with a subsequent (or top) support layer. In some embodiments, the bottom outer surface of each of the distal (or opposing) ends of the geometrical layer is in contact with a preceding support layer. In some embodiments, the upper outer surface of each of the distal (or opposing) ends of the geometrical layer is in contact with a subsequent support layer. In some embodiments, the plurality of cylinders or fibers within the geometrical layer are bridged between two support layers, wherein the support layers are aligned within a vertical plane.

In some embodiments, a distance between subsequent support layers aligned within a vertical plane is at most 97%, at most 95%, at most 90%, at most 80%, at most 70%, at most 60% of a length of the geometrical layer. In some embodiments, a distance between subsequent support layers aligned within a vertical plane is at least 95%, at least 90%, at least 80%, at least 70%, at least 60%, at least 50% of a length of the geometrical layer.

In some embodiments, the support layer provides a mechanical support to the geometrical layer. In some embodiments, the support layer increases the mechanical strength of the template.

In some embodiments, at least 60%, at least 70%, at least 80%, at least 90% of the outer surface of the support layer is in contact with the geometrical layer. In some embodiments, at least 60%, at least 70%, at least 80%, at least 90% of the width of the support layer is in contact with or facing the plurality of fibers within the geometrical layer, wherein the width is an average length of the plurality of fibers within the support layer.

In some embodiments and as exemplified by FIG. 2C, a plurality of cylindrically shaped parallel fibers within the geometrical layer and a plurality of cylindrically shaped parallel fibers within the support layer are aligned perpendicular.

In some embodiments, the geometrical layer comprises parallel aligned fibers. In some embodiments, the fibers are in a form of parallel aligned cylinders.

In some embodiments, the cylinders within the geometrical layer have a diameter in the range of 50 μm to 400 μm. In some embodiments, the cylinders within the geometrical layer have a diameter in the range of 50 μm to 350 μm, 50 μm to 300 μm, 50 μm to 270 μm, 50 μm to 100 μm, 100 μm to 150 μm, 150 μm to 200 μm, 200 μm to 250 μm, 250 μm to 300 μm, 300 μm to 400 μm, 50 μm to 250 μm, 50 μm to 200 μm, 100 μm to 400 μm, 150 μm to 400 μm, 400 μm to 600 μm, 600 μm to 800 μm, 800 μm to 1000 μm, 1000 μm to 2000 μm, or 150 μm to 300 μm, including any range therebetween. In some embodiments, the diameter of the cylinder is compatible with a dimension (e.g. diameter or width) of a cell. In some embodiments, a value of the diameter is an average value.

In some embodiments, the support layer has a thickness in the range between 5 to 300 μm. In some embodiments, the cylinders within the support layer have a diameter of 5 μm to 200 μm, 5 μm to 150 μm, 10 μm to 200 μm, 20 μm to 200 μm, 30 μm to 200, 100 μm to 200 μm, 150 μm to 200 μm, 200 μm to 300 μm, 10 μm to 30 μm, 30 μm to 50 μm, 50 μm to 100 μm, 100 μm to 150 μm, μm, 30 μm to 150 μm, or 30 μm to 100 μm, including any range therebetween.

In some embodiments, the distance between the support layers in the vertical plane of the template is in the range of 50 μm to 50 mm. In some embodiments, the distance between the support layers in the vertical plane of the template is in the range of 50 μm to 350 μm, 50 μm to 300 μm, 50 μm to 270 μm, 50 μm to 250 μm, 50 μm to 200 μm, 100 μm to 400 μm, 150 μm to 400 μm, 300 μm to 1 mm, 300 μm to 3 mm, 300 μm to 20 mm, 50 μm to 1 mm, 50 μm to 10 mm, or 50 μm to 20 mm, including any range therebetween.

In some embodiments, the length of the geometrical layer is in the range of 1 μm to 50 mm, 1 to 10 μm, 10 to 30 μm, 30 to 50 μm, 50 μm to 350 μm, 50 μm to 300 μm, 50 μm to 270 μm, 50 μm to 250 μm, 50 μm to 200 μm, 50 to 100 μm, 100 μm to 400 μm, 150 μm to 400 μm, 400 μm to 1 mm, 300 μm to 3 mm, 300 μm to 20 mm, 300 μm to 10 mm, 100 μm to 10 mm, 50 μm to 1 mm, 50 μm to 10 mm, or 50 μm to 20 mm, including any range therebetween, wherein the length is as described herein. In some embodiments, the length of the geometrical layer is at most 15 mm, at most 12 mm, at most 10 mm, at most 5 mm, at most 1 mm, including any value or range therebetween.

In some embodiments, the distance between the subsequent cylinders within the geometrical layer is in the range of 1 to 200 μm, 1 to 5 μm, 5 to 10 μm, 10 to 15 μm, 15 to 20 μm, 20 to 30 μm, 30 to 50 μm, 50 to 100 μm, 100 to 200 μm, including any value or range therebetween.

In some embodiments, the 3D template or the template comprises a free space or lumen. In some embodiments, the lumen is defined by the plurality of subsequent or adjacent cylinders. In some embodiments, the lumen is defined by the plurality of subsequent or adjacent cylinders within two adjacent layers. In some embodiments, the lumen is defined by the plurality of subsequent cylinders within each of the geometric layer or the support layer. In some embodiments, the lumen is defined by the plurality of cylinders within the geometric layer and by the plurality of cylinders within the support layer. In some embodiments, the lumen is defined by the plurality of cylinders within a layer and by a plurality of adjacent layers.

In some embodiments, the 3D template or the template comprises a plurality of chambers. In some embodiments, each chamber defines a specific region within the template. In some embodiments, each chamber comprises at least one wall. In some embodiments, the wall further comprises an opening. In some embodiments, the wall is an exterior wall of the template. In some embodiments, the wall defines at least a part of the lumen of the template.

In some embodiments, the lumen or the space between the adjacent layers is substantially defined by a dimension (e.g. thickness) of the support layer. In some embodiments, the lumen or the space between the adjacent layers is substantially defined by a lumen between subsequent support layers within the vertical plane.

In some embodiments, the lumen or the space between the cylinders has a thickness in the range of 5 μm to 150 μm, 10 μm to 150 μm, 15 μm to 150 μm, 20 μm to 150 μm, 30 μm to 150 μm, or 30 μm to 100 μm, including any range therebetween.

In some embodiments, the ratio of a lumen volume to a total volume of the template is at least 1:10, at least 2:10, at least 3:10, at least 4:10, at least 5:10, at least 6:10, at least 7:10 including any value therebetween.

In some embodiments, the ratio of a lumen volume to a total volume of the template is at most 6:10, at most 5:10, at most 4:10, at most 3:10, including any value therebetween.

In some embodiments, the ratio of a lumen volume to a total volume of the template predetermines the stability of the template, wherein the stability is as described hereinabove.

Scaffold

In another aspect of the invention, there is a scaffold comprising a chamber, comprising at least one wall, wherein the wall comprises a biodegradable polymeric material, and wherein a wall defines a plurality of lumens forming a pattern within the scaffold. In some embodiments, the scaffold is a 3D scaffold. In some embodiments, the scaffold is an implant scaffold. In some embodiments, the scaffold is manufactured according to the method of the invention as described hereinabove. In some embodiments, the scaffold is manufactured by dissolving the template, thereby obtaining a 3D scaffold comprising a plurality of lumens defined by at least one wall.

In some embodiments, the shape of the scaffold is predetermined by the shape of the template. In some embodiments, the shape of the scaffold is according to an image of the target site, as described herein.

In some embodiments, the scaffold comprises a plurality of chambers wherein each chamber comprises a wall. In some embodiments, the plurality of chambers is organized in a pattern within the scaffold. In some embodiments, the plurality of chambers is oriented along a longitudinal axis of the scaffold. In some embodiments, the scaffold comprises a plurality of parallel chambers oriented along a longitudinal axis of the scaffold. In some embodiments, the chamber comprises an opening. In some embodiments, the chamber comprises a plurality of openings. In some embodiments, the chamber comprises a plurality of side openings. In some embodiments, the chamber comprises a first side opening and a second side opening, wherein the side openings are located at opposed (distal) ends of the chamber.

In some embodiments, the plurality of chambers is in a form of parallel hollow-shape cylinders. In some embodiments, a wall of the chamber defines a lumen, as described herein. In some embodiments, the plurality of chambers shares a common wall.

In some embodiments, at least 70%, at least 80%, at least 90%, at least 92%, at least 95%, at least 97%, at least 93%, at least 98%, at least 99% of the interior volume of the plurality of chambers is devoid of a polymeric material.

In some embodiments, the wall comprises a biodegradable polymeric material. In some embodiments, the biodegradable polymeric material is biodegradable polymeric precursor.

In some embodiments, the biodegradable polymer precursor comprises poly(lactic-co-glycolic acid), PLLA-co-PLGA, poly(lactic acid), poly(l-lactic acid) PLLA, poly(l-glycolic acid) PLGA, polycaprolactone, polydioxanone, polyvinyl alcohol (PVA), polyurethanes, polycarbonates, polyhydroxyalkanoates (polyhydroxybutyrates and polyhydroxyvalerates and copolymers), polysaccharides, polyhydroxyalkanoates polyglycolide-co-caprolactone, polyethylene oxide (PEG), polypropylene oxide (PPG), a compolymer of PPG and PEG, PEG-co-PLA, polyglycolide-co-trimethylene carbonate, including any combination or a compolymer thereof.

In some embodiments, the biodegradable polymer precursor comprises poly(lactic-co-glycolic acid), PLLA-co-PLGA, poly(lactic acid), poly(l-lactic acid) PLLA, poly(l-glycolic acid) PLGA, polycaprolactone, polydioxanone, polyurethanes, polycarbonates, polyhydroxyalkanoates (polyhydroxybutyrates and polyhydroxyvalerates and copolymers), polyhydroxyalkanoates, polyglycolide-co-caprolactone, polyethylene oxide (PEG), polypropylene oxide (PPG), PPG-co-PEG, PEG-co-PLA, polyglycolide-co-trimethylene carbonate, including any combination or a copolymer thereof.

In some embodiments, the biodegradable polymer precursor comprises poly(lactic-co-glycolic acid), PLLA-co-PLGA, poly(lactic acid), poly(l-lactic acid) PLLA, poly(l-glycolic acid) PLGA, a polyester, polycaprolactone, polydioxanone, polyurethanes, polycarbonates, polyhydroxyalkanoates (polyhydroxybutyrates and polyhydroxyvalerates and copolymers), polyhydroxyalkanoates, polyglycolide-co-caprolactone, polyethylene oxide (PEG), polypropylene oxide (PPG), PPG-co-PEG, PEG-co-PLA, polyglycolide-co-trimethylene carbonate, including any combination or a copolymer thereof.

In some embodiments, the biodegradable polymer precursor comprises poly(lactic-co-glycolic acid), PLLA-co-PLGA, poly(lactic acid), poly(l-lactic acid) PLLA, poly(l-glycolic acid) PLGA, a polyester, polycaprolactone, polydioxanone, polyurethanes, polycarbonates, polyhydroxyalkanoates (polyhydroxybutyrates and polyhydroxyvalerates and copolymers), polyhydroxyalkanoates, polyglycolide-co-caprolactone, PEG-co-PLA, polyglycolide-co-trimethylene carbonate, including any combination or a copolymer thereof. In some embodiments, the wall is devoid of a gel-forming polymer. In some embodiments, the wall is devoid of any of gelatin, nitrocellulose, methylcellulose, cellulose, PEG, poly(N-isopropylacrylamide). In some embodiments, the wall is devoid of a peptide, a polysaccharide (e.g. hyaluronic acid, chitosan, alginate, agarose).

In some embodiments, the polymer precursor comprises a biocompatible and biodegradable polymer precursor.

As used herein, the term "biocompatible" refers to a material or combination of materials can be contacted with cells, tissue in vitro or in vivo, or used with mammals or other organisms and has acceptable toxicological properties for contact and/or beneficial use with such cells, tissue, and/or animals. For example, a biocompatible material may be one that is suitable for implantation into a subject without adverse consequences, for example, without substantial toxicity or acute or chronic inflammatory response and/or acute rejection of the material by the immune system, for instance, via a T-cell response. It will be recognized that "biocompatibility" is a relative term, and some degree of inflammatory and/or immune response is to be expected even for materials that are highly compatible with living tissue. However, non-biocompatible materials are typically those materials that are highly toxic, inflammatory and/or are acutely rejected by the immune system, e.g., a non-biocompatible material implanted into a subject may provoke an immune response in the subject that is severe enough such that the rejection of the material by the immune system cannot be adequately controlled, in some cases even with the use of immunosuppressant drugs, and often can be of a degree such that the material must be removed from the subject. In some embodiments, biocompatible materials are those that are approved for use in humans by an appropriate regulatory agency, such as the Federal Drug Administration (FDA) in the United States; the European Commission (EC)/European Medicines Agency (EMEA) in Europe; or Health Products and Food Branch (HPFB) in Canada.

In some embodiments, the polymers can be modified by chemical or physical methods, such as cross-linking, heat treatment, photochemical treatment, and/or changes in the chemical or physical environment. In some embodiments, the polymer modification can occur to different degrees, potentially resulting in different materials or material responses, as appreciated by one of skill in the art. Surface alterations, such as differences in hydrophilicity, charge, or other physical properties, facilitate cell adhesion.

In some embodiments, the plurality of lumens is arranged in a pattern within the scaffold. In some embodiments, the pattern is a specific pattern. In some embodiments, the lumens are provided in a pattern of distinct groups within the scaffold. In some embodiments, the pattern of distinct groups or clusters of lumens may be either random or regular; in either instance the apertures in each distinct group or cluster may be randomly distributed therein.

In one aspect, the plurality of lumens has a cylindrical geometry. In some embodiments, the plurality of lumens has a cylindrical geometry oriented along a longitudinal axis of the scaffold.

Figure 3A:
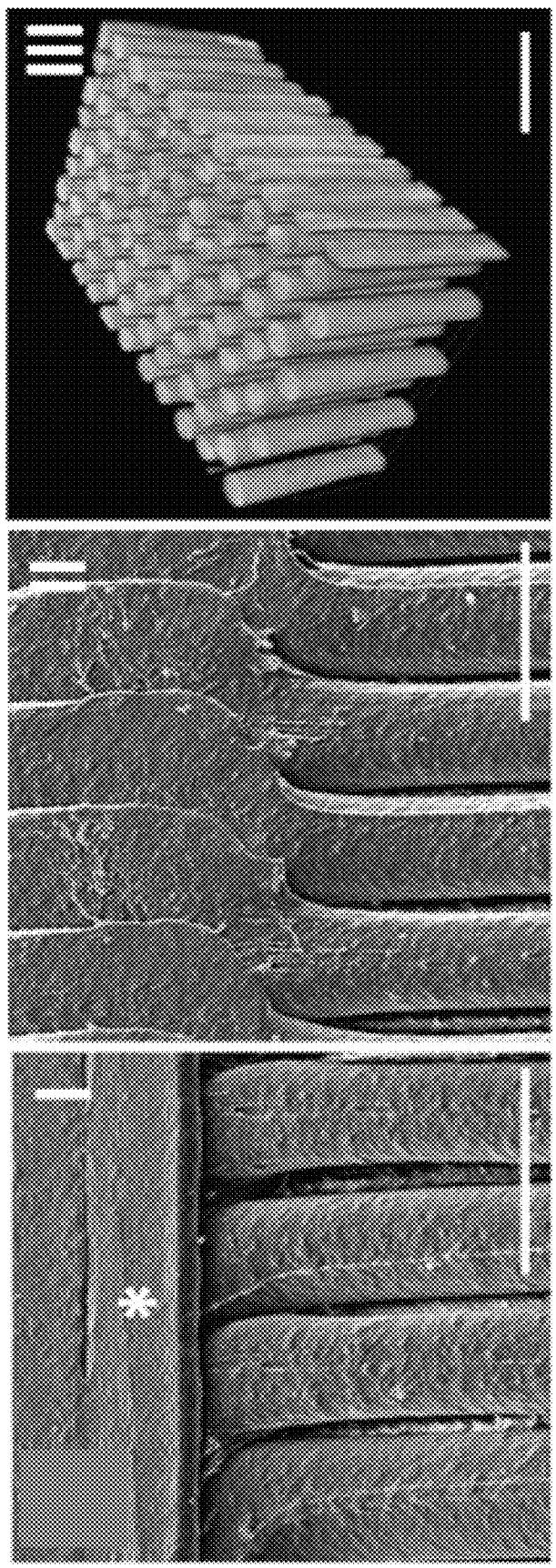
Figure 3B:
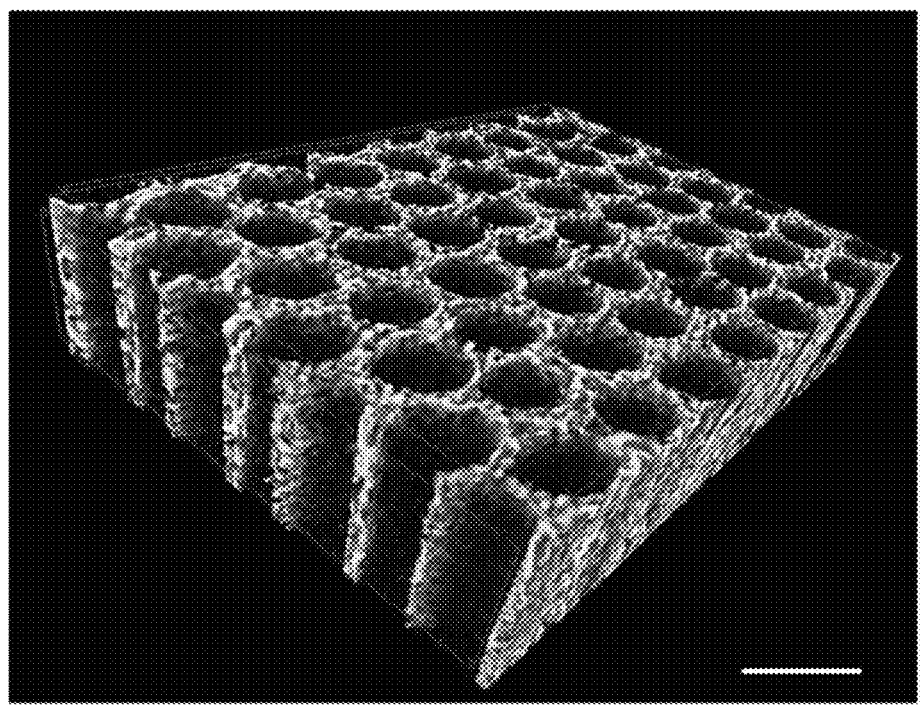

Reference is now made to FIG. 3B representing μCT image of an exemplary scaffold. In some embodiments, the scaffold comprises a plurality of parallel lumens oriented along a longitudinal axis of the scaffold, wherein the lumens are defined by the wall. In some embodiments, the scaffold comprises a plurality of hollow cylinders surrounded by at least one wall. In some embodiments, the scaffold comprises a plurality of hollow channels defined by the wall.

In some embodiments, the scaffold comprises a plurality of layers. In some embodiments, the scaffold comprises a plurality of vertically aligned layers. In some embodiments, each of the plurality of layers comprises a plurality of parallel lumens oriented along a longitudinal axis of the scaffold. In some embodiments, the lumens within the layer are in form of arrays oriented along a longitudinal axis of the scaffold. In some embodiments, the lumens have a cylindrical geometry. In some embodiments, the lumen has a plurality of opposed ends, corresponding to the openings of the chamber as described herein.

In some embodiments, the plurality of lumens has a geometry and/or pattern corresponding substantially the geometry and/or pattern of the plurality of arrays or fibers within the template as described hereinabove. In some embodiments, the plurality of lumens is in a form of parallel arrays oriented along a longitudinal axis of the scaffold. In some embodiments, the plurality of arrays has a cylindrical shape.

In some embodiments, the plurality of arrays is in a form of a plurality of aligned channels. In some embodiments, the plurality of aligned channels is oriented along a longitudinal axis of the scaffold. In some embodiments, the plurality of parallel aligned channels is oriented along a longitudinal axis of the scaffold. In some embodiments, the plurality of channels have a diameter in the range of 50 μm to 400 μm. In some embodiments, the plurality of channels have a diameter in the range of 120 μm to 400 μm. In some embodiments, the plurality of channels have a diameter in the range of 120 μm to 300 μm. In some embodiments, a diameter of channels is in the range of 50 μm to 350 μm, 50 μm to 300 μm, 50 μm to 250 μm, 50 μm to 100 μm, 100 μm to 110 μm, 110 μm to 400 μm, 110 μm to 300 μm, 110 μm to 260 μm, 150 μm to 400 μm, 150 μm to 300 μm, 150 μm to 350 μm, 150 μm to 260 μm, 150 μm to 200 μm, 110 μm to 150 μm, 200 μm to 250 μm, 250 μm to 300 μm, 70 μm to 400 μm, 100 μm to 400 μm, 70 μm to 250 μm, or 50 μm to 200 μm, including any range therebetween.

As used herein the term "channels" refers to a lumen having entrances and exits, in the implant scaffold, that maintain 3D coordinates throughout the lesion site, matching natural host architecture. In some embodiments, the channels or lumens provide a support for cell growth within the scaffold. In some embodiments, the channels or lumens provide entrances and exits to axons in the implants. In some embodiments, the channels or lumens are substantially empty, i.e. at the interior lumen is devoid of a polymeric material. In some embodiments, at least 70%, at least 80%, at least 90%, at least 92%, at least 95%, at least 97%, at least 93%, at least 98%, at least 99% of the interior volume of the plurality of channels or lumens is devoid of a polymeric material. In some embodiments, at least 70%, at least 80%, at least 90%, at least 92%, at least 95%, at least 97%, at least 93%, at least 98%, at least 99% of the interior volume of the plurality of chambers is devoid of a polymeric material, wherein the wall of each chamber defines a lumen as described herein.

In some embodiments, the implant scaffold is configured to be in gas communication with the target site via a plurality of lumens or channels. In some embodiments, the channel in gas communication with the target site via the openings of the lumen, wherein the openings are side openings of the chamber, as described herein. In some embodiments, the implant scaffold is configured to be in a fluid communication with the target site via a plurality of lumens or channels. In some embodiments, at least 70%, at least 80%, at least 90%, at least 92%, at least 95%, at least 97%, at least 93%, at least 98%, at least 99% of the lumen is configured to be in gas communication or in fluid communication with the target site. In some embodiments, the channel in gas or fluid communication with the target site via a plurality of openings or pores in the wall.

As used herein, the terms "scaffold" and "implant" are used interchangeably and refer to the 3D printed structures with or without stem cells.

In some embodiments, a distance between the channels or lumens within each horizontal layer is predefined by a distance between fibers or arrays within the geometric layer of the template. In some embodiments, a distance between the layers of channels within the scaffold is predefined by a distance between subsequent geometric layers of the template. In some embodiments, a distance between the layers of channels within the scaffold is substantially the same as the thickness of the support layer of the template.

In some embodiments, the channels are separated by the polymeric material, wherein the polymeric material is as described hereinabove. In some embodiments, the polymeric material has a thickness in the range of 5 µm to 150 µm, 10 µm to 150 µm, 15 µm to 150 µm, 20 µm to 150 µm, 30 µm to 150 µm, or 30 µm to 100 µm, including any range therebetween.

In some embodiments, a ratio of a total volume of the plurality of lumens or channels to a total volume of the scaffold is at least 30%, at least 40%, at least 50%, at least 60%, at least 70%, including any range or value therebetween. In some embodiments, a ratio of a total volume of the plurality of lumens or channels to a total volume of the scaffold is between 30 and 70%, between 30 and 40%, between 40 and 50%, between 40 and 60%, between 45 and 55%, between 55 and 60%, between 60 and 70% including any range or value therebetween.

In some embodiments, the scaffold comprises an exterior wall. In some embodiments, the exterior wall maintains substantially the shape or geometry of the template. In some embodiments, the exterior wall has a shape or geometry compatible with a shape of the target site (e.g. lesion). In some embodiments, the shape of the exterior wall of the scaffold is characterized by at least 80%, at least 85%, at least 90%, at least 92%, at least 95%, at least 97%, at least 99% identity with a shape of the target site (e.g. lesion). In some embodiments, the shape as used herein is a 3D structure. In some embodiments, a 3D structure of the exterior wall of the scaffold is characterized by at least 80%, at least 85%, at least 90%, at least 92%, at least 95%, at least 97%, at least 99% identity with a 3D structure of the target site (e.g. lesion). In some embodiments, a dimension of the exterior wall of the scaffold is compatible with a dimension of the target site (e.g. lesion). In some embodiments, a dimension of the exterior wall of the scaffold is characterized by at least 80%, at least 85%, at least 90%, at least 92%, at least 95%, at least 97%, at least 99% identity with a dimension of a lesion site, as provided by an image of the lesion site. In some embodiments, a standard deviation of a dimension of the exterior wall from a dimension of a lesion site, as provided by a 3D image is at most 10%, at most 8%, at most 5%, at most 3%, at most 2%, at most 1%, at most 0.1% including any value therebetween.

In some embodiments, the wall of the scaffold is a porous wall. In some embodiments, the wall comprises a plurality of pores. In some embodiments, the wall comprises a plurality of pores. In some embodiments, a total volume of the plurality of pores to a total volume of the scaffold is at least 30%, at least 40%, at least 50%, at least 60%, at least 70%, including any range or value therebetween. In some embodiments, a ratio of a total volume of the plurality of pores to a total volume of the scaffold is between 30 and 70%, between 30 and 40%, between 40 and 50%, between 40 and 60%, between 45 and 55%, between 55 and 60%, between 60 and 70% including any range or value therebetween.

In some embodiments, the plurality of pores is characterized by an average pore diameter of less than 100 µm, less than 80 µm, less than 70 µm, less than 60 µm, less than 50 µm, less than 40 µm, less than 35 µm including any range or value therebetween.

In some embodiments, the plurality of pores is characterized by an average pore diameter between 10 and 100 µm, between 10 and 20 µm, between 20 and 30 µm, between 30 and 35 µm, between 35 and 40 µm, between 40 and 45 µm, between 45 and 50 µm, between 50 and 60 µm, between 60 and 80 µm, between 80 and 100 including any range or value therebetween.

In some embodiments, the wall comprises a plurality of internal pores and external pores that are open to one another and form continuous flow paths or channels through the wall.

In some embodiments, the implant scaffold has a total porosity in the range of 90% to 99%, 91% to 99%, 92% to 99%, 93% to 99%, 94% to 99%, or 95% to 99%, including any range therebetween.

In some embodiments, the implant scaffold has a porosity of more than 90%. In some embodiments, the implant scaffold has a porosity in the range of 90% to 99%, 91% to 99%, 92% to 99%, 93% to 99%, 94% to 99%, or 95% to 99%, including any range therebetween. In some embodiments, the implant scaffold has a porosity of about 97%, wherein about is as described herein.

In some embodiments, the implant scaffold is highly porous. In some embodiments, a highly porous implant scaffold refers to a scaffold for example, having a porosity of greater than 1% to less than or equal to 99%, or having a porosity of greater than 10% to less than or equal to 97%.

In some embodiments, the pore diameter and/or total porosity of the scaffold is predetermined by the fabrication conditions. In some embodiments, the pore diameter and/or total porosity of the scaffold is predetermined by the exact conditions of solvent evaporation (such as by freeze drying). In some embodiments, the pore diameter and/or total porosity of the scaffold is predetermined by the concentration of the polymeric precursor in the solution as described hereinabove.

In some embodiments, the length of the implant scaffold corresponds to the length of anchor to anchor in each margin. According to the present invention, anchors size, spacing and shape can be chosen to obtain custom-made implant scaffolds.

In some embodiments, the implant scaffold is personalized to a subject. In some embodiments, the implant scaffold can provide "custom fit" implants for individual target site such as subject lesions.

In some embodiments, the implant scaffold supports neural tissue growth, connective tissue growth, muscular tissue growth, or any combination thereof.

As used herein, the terms "pore" and "pores" refer to pores of various sizes, including so-called "macropores" (pores greater than 50 nm diameter), "mesopores" (pores having diameter between 2 nm and 50 nm), and "micropores" (pores having diameter of less than 2 nm), where the pore size refers to an average or median value, including both the internal and external pore diameter sizes.

In some embodiments, the scaffold is in a form of a 3D array comprising a plurality of aligned shapes.

In some embodiments the aligned shapes comprise cylinders having a diameter in the range of 50 µm to 400 µm, 50 µm to 350 µm, 50 µm to 300 µm, 50 µm to 250 µm, 70 µm to 400 µm, 100 µm to 400 µm, 70 µm to 250 µm, or 50 µm to 200 µm, including any range therebetween.

In some embodiments, the shapes or lumens are separated by the polymeric material, wherein the polymeric material is as described hereinabove. In some embodiments, polymeric material has a thickness as described hereinabove.

In some embodiments, the polymeric material separates the channels in the form of walls. In some embodiments, the walls comprise a plurality of pores, wherein the pores are as described herein.

In some embodiments, the scaffold is further coated with fibronectin prior to cell seeding and implantation in the target site. In some embodiments, the wall (e.g. the interior wall) of the scaffold is further coated with fibronectin. In some embodiments, fibronectin coating is for promoting cell adhesion and/or proliferation.

In some embodiments, an implant scaffold as described herein promotes cell adhesion. In some embodiments, an implant scaffold as described herein promotes cell growth, proliferation, differentiation, repair, and/or regeneration. In some embodiments, the tissue is a neural tissue, such as axons. In some embodiments, the dimension and the orientation (along a longitudinal axis) of the plurality of channels within the scaffold promotes axon growth. In some embodiments, the porosity of the wall predetermines cell growth, proliferation, differentiation, repair, and/or regeneration. Without being bound to any particular theory or mechanism, it is postulated that the channel diameter, channel orientation and the 3D pattern of the plurality of channels, as described herein advantageous for promoting cell growth, proliferation, differentiation, repair, and/or regeneration, as represented by FIGS. 4-7. Additionally, it is postulated that the side openings (pores) within one or more walls of the scaffold, having a narrow distribution profile (as represented by FIG. 3G) are advantageous for promoting cell growth, proliferation, differentiation, repair, and/or regeneration, as specifically exemplified for axons (FIGS. 4-7). Additionally, it is postulated that promotion of cell growth, proliferation, differentiation, repair, and/or regeneration, as exemplified herein may be related to improved fluid exchange and optimized mechanical properties of the porous scaffold of the invention.

In some embodiments, the implant scaffold is configured to support cell adhesion. In some embodiments, the implant scaffold is configured to support cell proliferation and/or cell growth.

By "promoting" cell growth, cell proliferation, cell differentiation, cell repair, or cell regeneration, it is meant that a detectable increase occurs in either a rate or a measurable outcome of such processes occurs in the presence of the implant scaffold according to the present invention as compared to a cell or organism's process in the presence of a control implant scaffold.

In some embodiments, the implant scaffold has a Young's modulus in the range of 10 Kpa to 5000 Kpa. In some embodiments, the implant scaffold has a Young's modulus in the range of 10 Kpa to 5000 Kpa, 100 Kpa to 5000 Kpa, 200 Kpa to 5000 Kpa, 500 Kpa to 5000 Kpa, 1000 Kpa to 5000 Kpa, 2000 Kpa to 5000 Kpa, 10 Kpa to 2000 Kpa, 10 Kpa to 1000 Kpa, or 10 Kpa to 500 Kpa, including any range therebetween.

In some embodiments, "Young's modulus" refers to an elastic modulus. In some embodiments, the phrase "elastic modulus" is determined by response of a material to application of tensile stress (e.g., according to procedures known in the art).

In some embodiments, the polymeric material comprises two biodegradable polymers.

In some embodiments, the implant scaffold is for use in muscle and nerve regeneration.

According to some embodiments, the present invention provides an implant scaffold comprising a water-soluble template in the form of a 3D geometrical array and a polymeric material.

In some embodiments, the implant scaffold comprises residual amounts of an organic solvent.

In some embodiments, the polymeric material comprises two biodegradable polymers.

In some embodiments, the implant scaffold is for use in muscle and nerve regeneration.

According to some embodiments, the present invention provides an implant scaffold comprising a plurality of aligned channels having a diameter in the range of 50 µm to 400 µm, wherein the channels are separated by a porous wall comprising a polymeric material and having a thickness in the range of 5 µm to 150 µm.

In some embodiments, the implant scaffold has a Young's modulus in the range of 10 Kpa to 5000 Kpa. In some embodiments, the implant scaffold has a Young's modulus in the range of 10 Kpa to 5000 Kpa, 100 Kpa to 5000 Kpa, 200 Kpa to 5000 Kpa, 500 Kpa to 5000 Kpa, 1000 Kpa to 5000 Kpa, 2000 Kpa to 5000 Kpa, 10 Kpa to 2000 Kpa, 10 Kpa to 1000 Kpa, or 10 Kpa to 500 Kpa, including any range therebetween.

In some embodiments, the scaffold is sufficiently stable (i.e. maintains its structural integrity) to support cell growth. In some embodiments, the mechanical properties (e.g. Young's modulus) of the scaffold are sufficient for providing a support for cell growth. In some embodiments, the mechanical properties (e.g. Young's modulus) of the scaffold are sufficient for use thereof as an implant. In some embodiments, the mechanical properties of the scaffold are compatible with surgical handling. In some embodiments, surgical handling properties of the scaffold are sufficient for use thereof as an implant in a subject in need thereof (e.g. for regeneration of neural tissue). In some embodiments, the mechanical properties (e.g. Young's modulus) of the scaffold are compatible with the mechanical properties of the target site. In some embodiments, the Young's modulus of the scaffold is compatible with the Young's modulus of the tissue (e.g. nerve tissue) at the site of lesion. In some embodiments, the Young's modulus of the scaffold is predetermined by the concentration of the polymeric precursor in the solution as exemplified by FIG. 3J. In some embodiments, the Young's modulus of the scaffold is predetermined by the porosity of the scaffold (FIG. 3E).

In some embodiments, the scaffold is sufficiently stable (i.e. substantially maintains its structural integrity, as described herein) within the target site. In some embodiments, the scaffold is sufficiently stable within the target site for at least 1 day (d), at least 5 d, at least 10 d, at least 15 d, at least 20 d, at least 25 d, at least 30 d, at least 35 d, at least 40 d, at least 50 d, at least 60 d, at least 70 d, at least 90 d, at least 120 d including any range or value therebetween, wherein stable is as described herein.

In some embodiments, the implant scaffold has a total porosity in the range of 90% to 99%, 91% to 99%, 92% to 99%, 93% to 99%, 94% to 99%, or 95% to 99%, including any range or value therebetween.

In some embodiments, a ratio between total volume of the plurality of side openings (pores) to a total volume of the polymeric material within the scaffold is between 5:1 and 20:1, is between 5:1 and 7:1, is between 7:1 and 10:1, is between 10:1 and 13:1, is between 11:1 and 13:1, is between 13:1 and 15:1, is between 15:1 and 17:1, is between 17:1 and 20:1, including any range therebetween, wherein side openings refer to a plurality of pores within the wall, as described herein. FIG. 3I represents a percentage of a total pore volume, a total channel volume and a total volume of the polymeric material relative to a total volume of the scaffold.

In some embodiments, the implant scaffold or the scaffold is characterized by a wall porosity between 80 and 99%, between 80 and 85%, between 85 and 90%, between 90 and 95%, between 90 and 93%, between 93 and 95%, between 95 and 99% including any range therebetween.

In some embodiments, the implant scaffold or the scaffold is rigid (i.e. substantially maintains its structural integrity, as described herein). In some embodiments, the rigidity of the scaffold is defined by the Young's modulus. In some embodiments, the rigidity of the scaffold is predetermined by manufacturing conditions, such as by the concentration of the polymeric precursor in the solution, as described herein.

In some embodiments, the implant scaffold or the scaffold is substantially devoid of swelling upon contacting the scaffold with an aqueous solution or with the target site, wherein substantially is as described herein. In some embodiments, swelling as used herein relates to increase of a dimension (e.g. volume) and/or mass of the scaffold. In some embodiments, the scaffold is characterized by at most 10%, at most 8%, at most 5%, at most 3%, at most 2%, at most 1%, at most 0.5%, at most 0.1%, at most 0.01% swelling upon contact with water or with the target site, wherein swelling is as described herein.

In some embodiments, the implant scaffold comprises residual amounts of the releasable polymer (e.g. a water-soluble polymer). In some embodiments, the implant scaffold comprises residual amounts of butenediol vinyl alcohol (BVOH), polyvinyl alcohol (PVA), or both. In some embodiments, the polymeric material comprises two biodegradable polymers.

In some embodiments, the implant scaffold is for use in muscle and nerve regeneration. In some embodiments, the implant scaffolds can be used to promote axonal regeneration after spinal cord or peripheral nerve injury.

In some embodiments, the implant scaffolds according to the present invention have a length of about 1 mm, about 2 mm, about 3 mm, about 4 mm, about 5 mm, about 6 mm, about 7 mm, about 8 mm, about 9 mm, about 10 mm, about 20 mm, about 30 mm, about 40 mm, about 50 mm, including any value therebetween. In some embodiments, the implant scaffolds according to the present invention have a length between 1 mm to 4 mm, between 2 mm to 10 mm, or between about 1 mm to 20 mm, including any range therebetween.

General

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

3D Printing 3D printed templates were designed in SolidWorks and sliced in 3D slicer Prusa version. Mat lab was used to edit the g code files in order to match the bridging pattern to the anatomical reconstruction. The resulting constructs were composed of linear fiber arrays in the shape of the scaffolds, surrounded by a confounding solid perimeter. Each printed construct included three regions of aligned fibers in order to generate three multi-channel scaffolds. Each region of aligned fibers was individually sealed by a confounding perimeter and included one inlet channel for polymer solution injection.

The 3D STL file was imported to SolidWorks, converted to solid part and smoothed using the spline tool. The 3D anatomical reconstruction was used to prepare oriented printed constructs in the shape and size of the spinal cord lesion surrounded by a confounding perimeter and included an inlet channel for polymer solution injection. Rectangular scaffolds used in in vitro studies were designed to have the same thickness as anatomical scaffolds. Fiber arrays for in vitro study scaffolds measured 4×2.9×1.5 mm.

All constructs were printed on an i3 MK2.5 desktop printer (Prusa) modified with a 0.25 mm nozzle. Constructs were printed from water-soluble BVOH (Verbatim). Print settings and parameters for scaffolds are listed in Table 1:

| | |
|---|---|
| Fiber printing speed | 5 mm/sec |
| First layer printing speed | 10 mm/sec |
| Perimeter printing speed | 10 mm/sec |
| Solid infill printing speed | 30 mm/sec |
| Nozzle diameter | 250 µm |
| Fiber layer height | 200 µm |
| Side support layer height | 50 µm |
| Lateral width of extrusion | 250 µm |
| Lateral distance between fibers | 70 µm |
| Fan speed | 70% |
| Extruder temperature | 210° C. |
| Stage temperature | 60° C. |

Scaffold Fabrication

PLLA (Polysciences) and PLGA (Boehringer-Ingelheim) were each separately dissolved in dioxane to yield a 7% (w/v) solution. PLLA solution was heated to 70° C. for 4 h, to completely dissolve the polymer. Both solutions were mixed in a ratio of 1:1. PLLA/PLGA solutions were injected into 3D-printed constructs through their inlet channels. The solution-loaded constructs were centrifuged at 100 rcf for 30 s, to ensure even spread of the solution into the construct. Loaded constructs were placed in a freezing container (Thermo Fisher Scientific) filled with isopropyl and placed in −80° C. to achieve gradual freezing, which improves pore size uniformity. This step was followed by lyophilization overnight. The constructs were then dissolved in distilled water for 6 h and dried at room temperature. Access polyester which adhered to the confounding perimeter was removed using forceps. Scaffolds were stored under vacuum until usage. Prior to cell/fibrin seeding, scaffolds were sterilized in a 70% ethanol solution.

PLLA/PLGA (1:1) scaffolds with random pore orientation were fabricated as follows. PLLA and PLGA were dissolved in chloroform to achieve a solution of 5% (w/v) polymer, 0.24 ml of which was casted into Teflon molds containing 0.4 g sodium chloride particles. The solvent was evaporated, and scaffolds were washed for 8 h in distilled water to leach the salt. Scaffolds were cut into 4 mm-diameter disks prior to µCT imaging.

For 3D anatomical reconstructions, a single rat underwent a T10 complete transection and was MRI-scanned 3 days after injury, under anesthesia (9.4T bore scanner, Bruker Biospec). Using CTan (Bruker), tiff file data sets of the anatomical scan were used to generate an STL file which approximated the lesion size and shape. To accomplish this, in one axial plane of the intact spinal cord adjacent to the lesion, pixels that represented spinal tissue were isolated using the thresholding tool and the region of interest tool. The resulting image was applied on every plane in which the lesion was detected, in order to generate a 3D approximation of missing tissue between the two disconnected stumps of the spinal cord. Micro CT (Bruker) and SEM (FEI) were used to image scaffolds and templates. Diffusion assays were performed in the micro CT after a one incubation of the samples in Iodine solution. Porosity was analyzed using Imaris and CTan (Bruker). The Young's modulus was measured in the assistance of a biodynamic test instrument (Bose).

For cell seeding, cells were suspended in a fibrin matrix (Omrix). 10-20 ul of suspension were injected to the scaffold. Scaffolds were implanted into a complete T10 spinal cord transection. Spinal cord was extracted after 4 weeks in vivo.

Statistical tests were carried out with Prism (GraphPad) which was also used to prepare all bar graphs. All error bars refer to standard error of the mean. For measurements of mechanical properties, one-way ANOVA tests were applied. For all other measurements, Student's t-test was used.

Example 1

Implant Fabrication and Micro Patterning of Biodegradable Scaffolds

Extrusion 3D printing often employs a rectilinear lattice pattern where the orientation of each additional layer is shifted by 90 degrees (FIG. 2A, "standard lattice"). This process generates fully isotropic constructs that are less compatible with linearly oriented tissues, e.g., skeletal muscles and nerves, however, is usually required to stabilize printed multi-layer structures. To generate an oriented topography, a layer-by-layer pattern was designed producing unidirectional fiber arrays, which later served as sacrificial constructs (FIG. 2A, "fiber array"). The first layer was composed of two support structures. The second layer was composed of linearly oriented fibers bridged between the support structures. These two layers were repeatedly printed one after the other to produce a linear array of oriented fibers. To stabilize printed fibers and prevent them from collapsing during extrusion, a high-speed printing fan was applied which rapidly solidified the extruded fibers even when printed over long distances. To demonstrate the feasibly of printing fiber arrays, butenediol vinyl alcohol (BVOH) copolymer was used to print fibers at different lengths of up to 10 mm. Due to its hydroxyl group, BVOH is water-soluble and can be used as a sacrificial material. In addition, it was found that it can be printed with very high precision. When visualized using microcomputed tomography (µCT), BVOH fiber arrays appeared highly ordered (FIG. 2C), with no observable collapsing fibers at any tested length. FIG. 2 shows schemes of the fabrication concept and micro patterning of biodegradable scaffolds.

3D printed water-soluble constructs are loaded with polymer solution followed by gradual freezing and lyophilazation of the solvent. The 3D printed construct is then dissolved in water to generate linearly oriented guidance channels (FIG. 1A).

Butenediol vinyl alcohol (BVOH) fibers are bridged in the air between anchors without support from bellow, to generate a spaced micro-array of linear fibers. Fiber layer thickness is 200 μm while anchor layer thickness is 50 μm (FIG. 1B). FIGS. 1B-C show the slicing of 3D printed structures: polymer solution inlet channels are pointed by arrows (FIG. 1C) and bridged fibers in confound cavities are pointed by arrows (FIG. 1D).

Figure 2B:
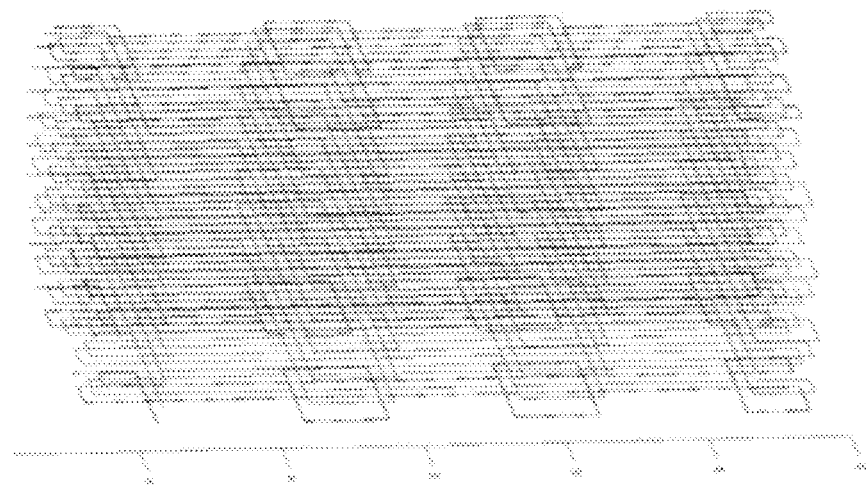
Figure 2C:
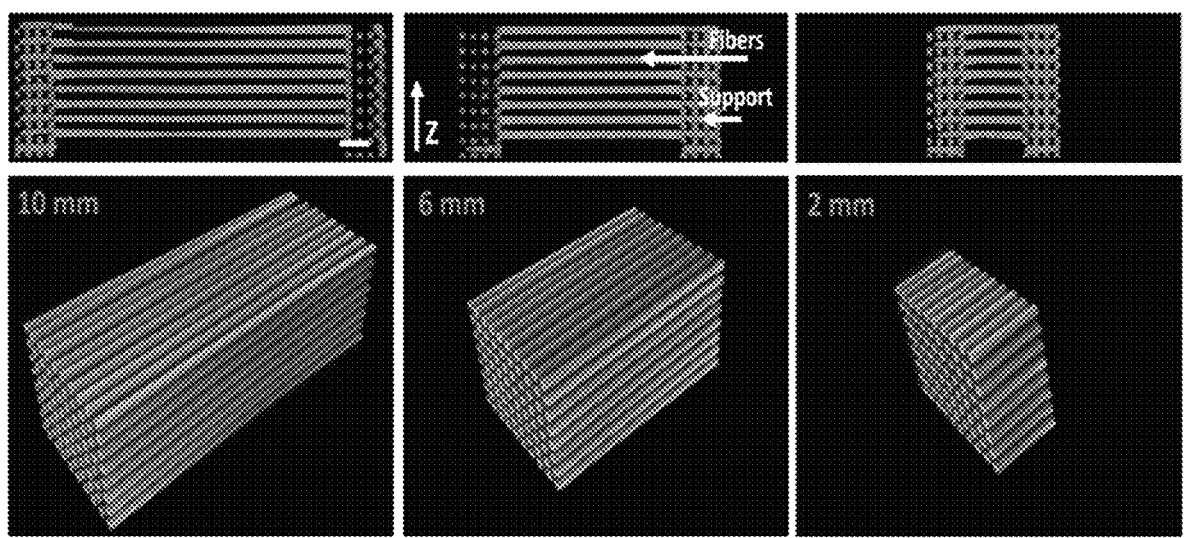

FIGS. 2A-B present a scheme of the pattern formation. In standard rectilinear printing pattern, all spaces between fibers are interconnected. In the micro-bridging technique described herein, the space where the polymer solution is casted into (scaffold area) is separated from the rest of the template and aligned arrays of micro-fibers are formed within this space. FIG. 3B presents the micro-fiber bridged location in 3D.

Example 2

Implant Scaffold Characterization

FIG. 3A shows SEM micrographs (IX) and μCT imaging (III) of BVOH template. The asterix marks the printed anchor on which the following bridged fibers will be printed. The bridged fibers layer is confounded on the margin to define the scaffold's border.

The microchannel scaffolds (1.5 mm thickness) had a mean total porosity of 96.52±0.89%, which was significantly higher than that of the control scaffolds (92.48±0.64). The pore diameters in 3D reconstructions of the two scaffold types were characterized (FIG. 3G). Control scaffolds had a normal pore diameter distribution, with different pore sizes randomly distributed throughout the scaffold (FIG. 3G-I). In contrast, porous microchannels showed a hierarchical two-peak distribution of pore sizes due to combined presence of microchannels and smaller interconnecting pores resulting from freeze-drying (FIG. 3G-II). The interconnecting pore diameter peaked at 32 μm, while the aligned channel diameters peaked at 240 μm and comprised 53.07±3.00% of the entire scaffold volume (FIG. 3I). Since interconnecting pores measured <100 μm in diameter, The described pore hierarchy is likely beneficial for simultaneous promotion of axonal growth in aligned regions and maintenance of porous walls to improve fluid exchange and optimize mechanical properties.

To quantify the effect of interconnecting pores on the mechanical properties of the scaffold, non-porous samples of PLLA/PLGA were prepared and compared their Young's modulus to freeze-dried PLLA/PLGA samples at concentrations of 3%, 5% and 7% w/v in dioxane. All samples were isotropic and fabricated without microchannels. As expected, the introduced porosity led to a dramatic reduction in the sample's Young's modulus by ~1-2 orders of magnitude, depending on the polymer's concentration in solution (FIG. 3J). For the fabrication of porous channel scaffolds a 7% w/v solution were chosen since it generated scaffolds with similar mechanical properties to spinal cord tissue. Furthermore, such scaffolds remained sufficiently firm for surgical handling, unlike scaffolds fabricated with lower concentrations of polymer.

FIG. 3B shows μCT imaging of the scaffold.

Figure 3C:
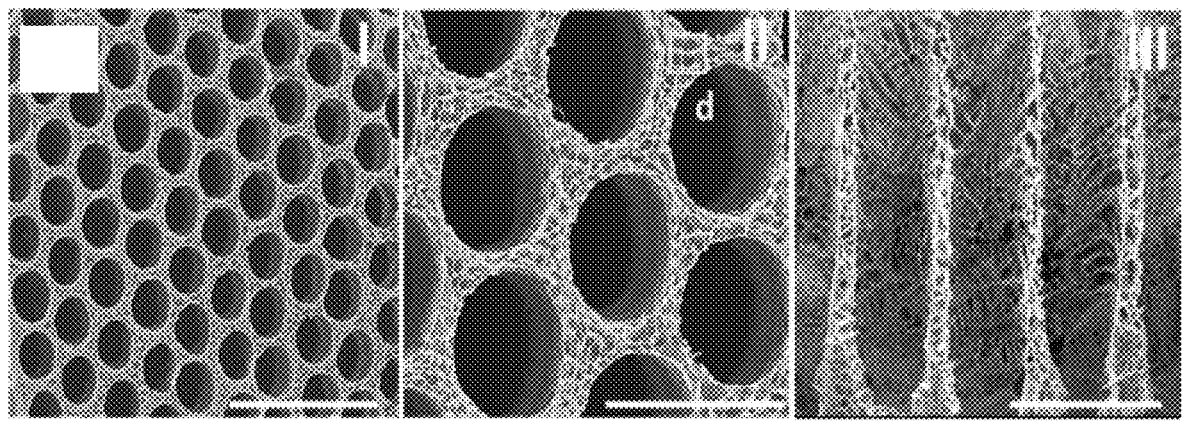

SEM micrographs of the scaffolds showing cross sections (IX) and longitudinal section (III) are presented in FIG. 3C. The mean wall diameter is 57.8 microns.

Figure 3D:
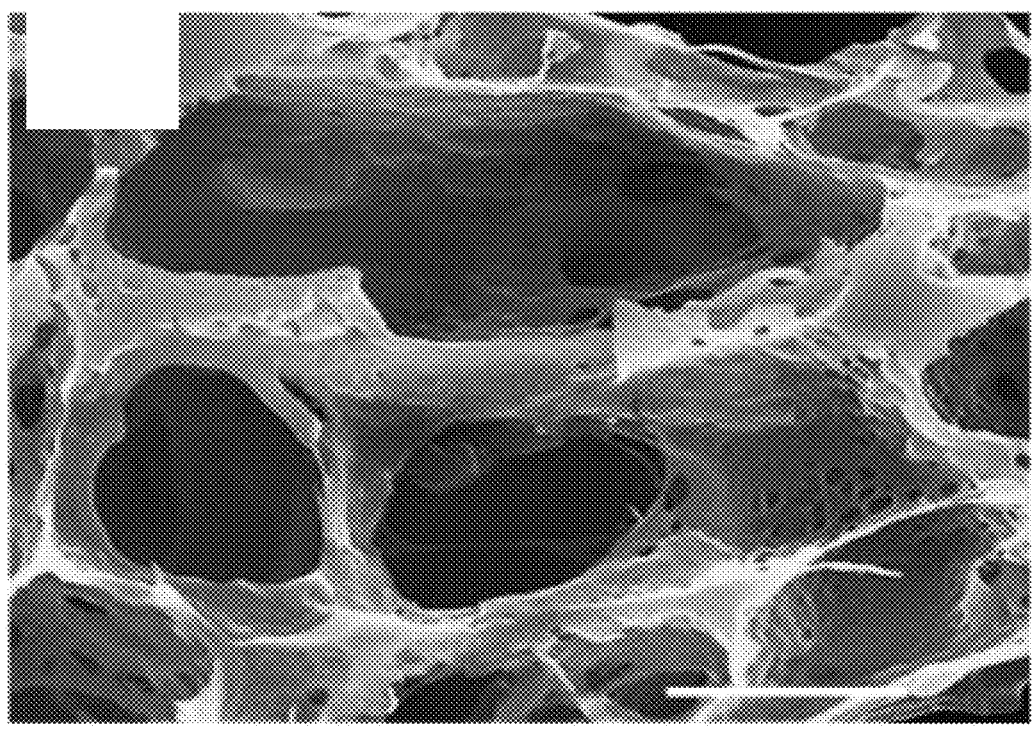
Figure 3E:
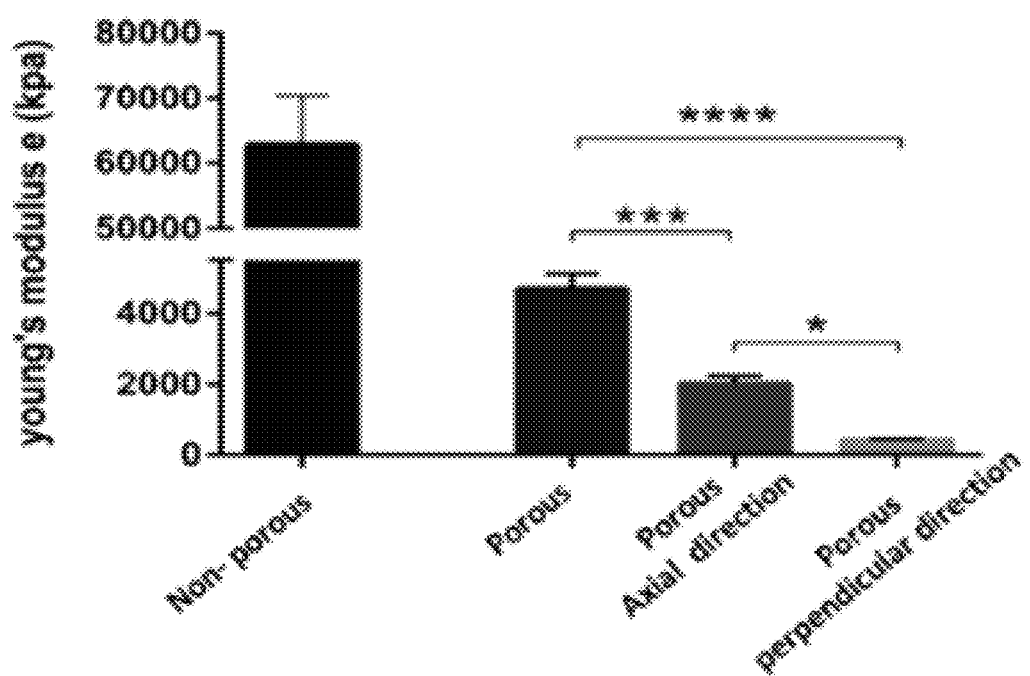

Picture of higher magnification showing pores in walls separating channels are presented in FIG. 3D.

FIG. 3E presents a bar graph showing the Young's modulus measurements of the scaffold.

Figure 3F:
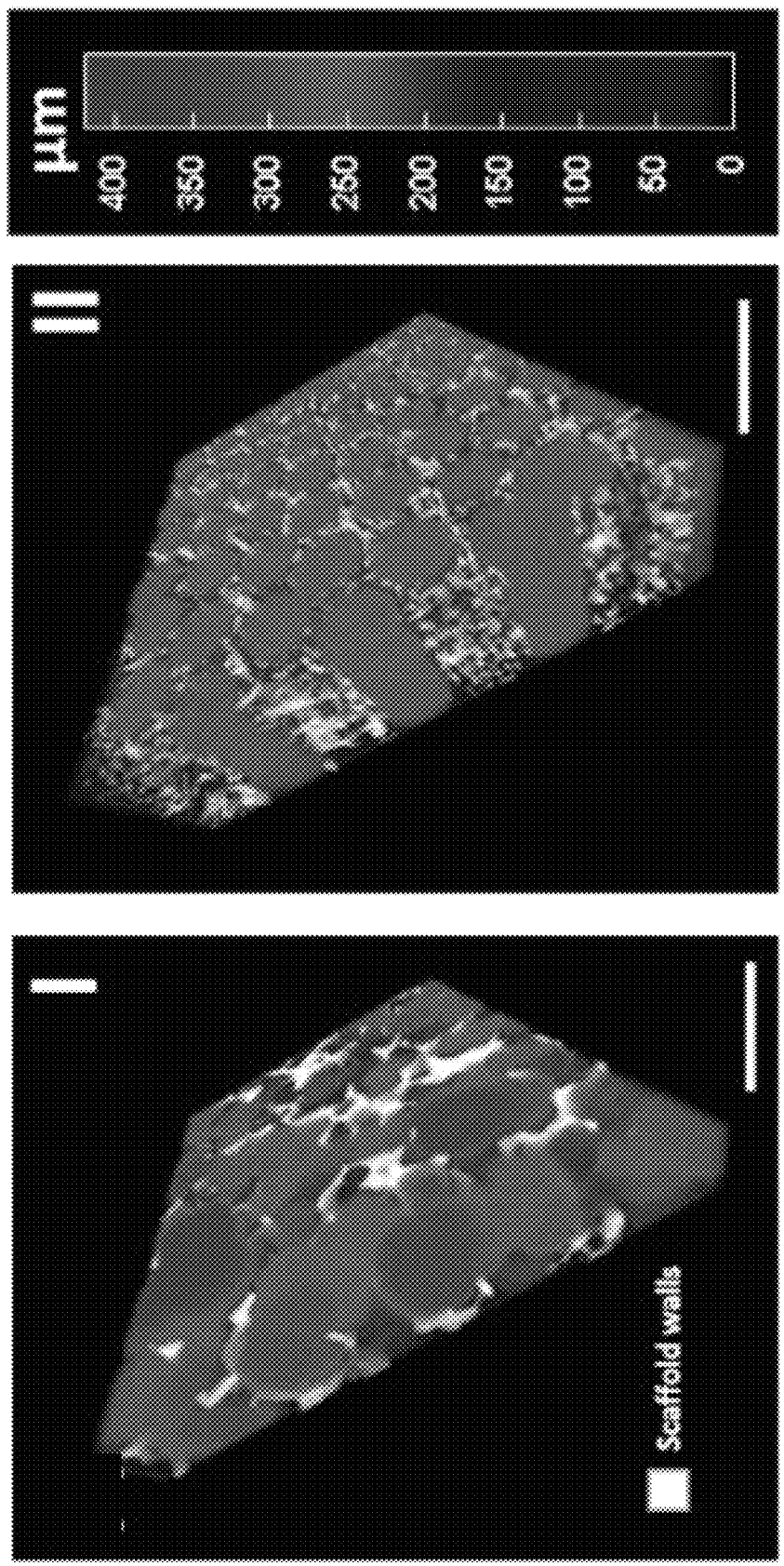
Figure 3H:
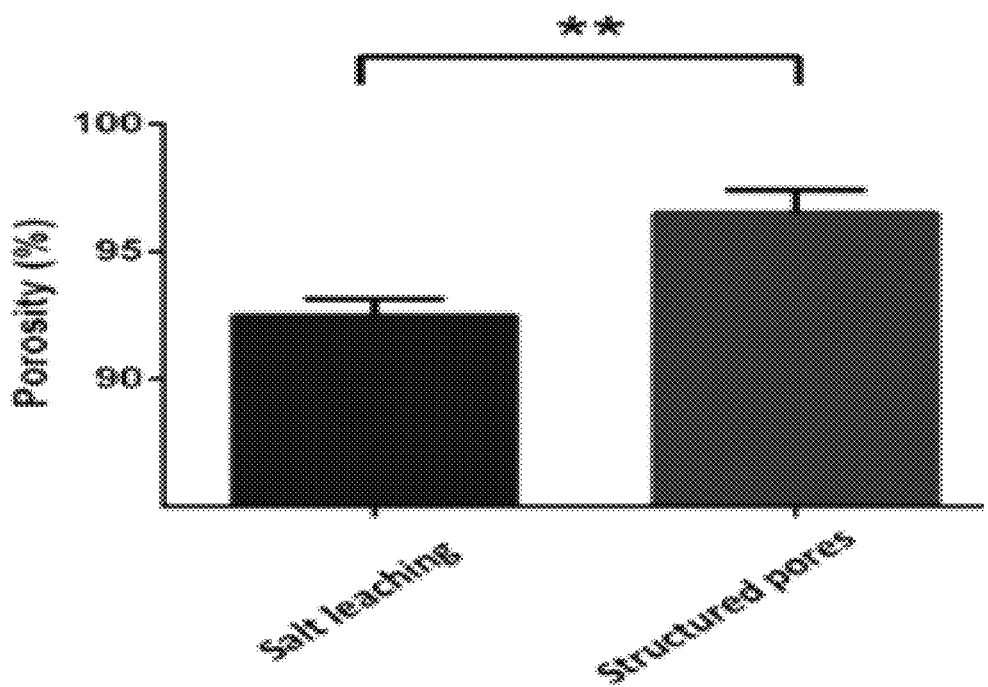
Figure 3I:
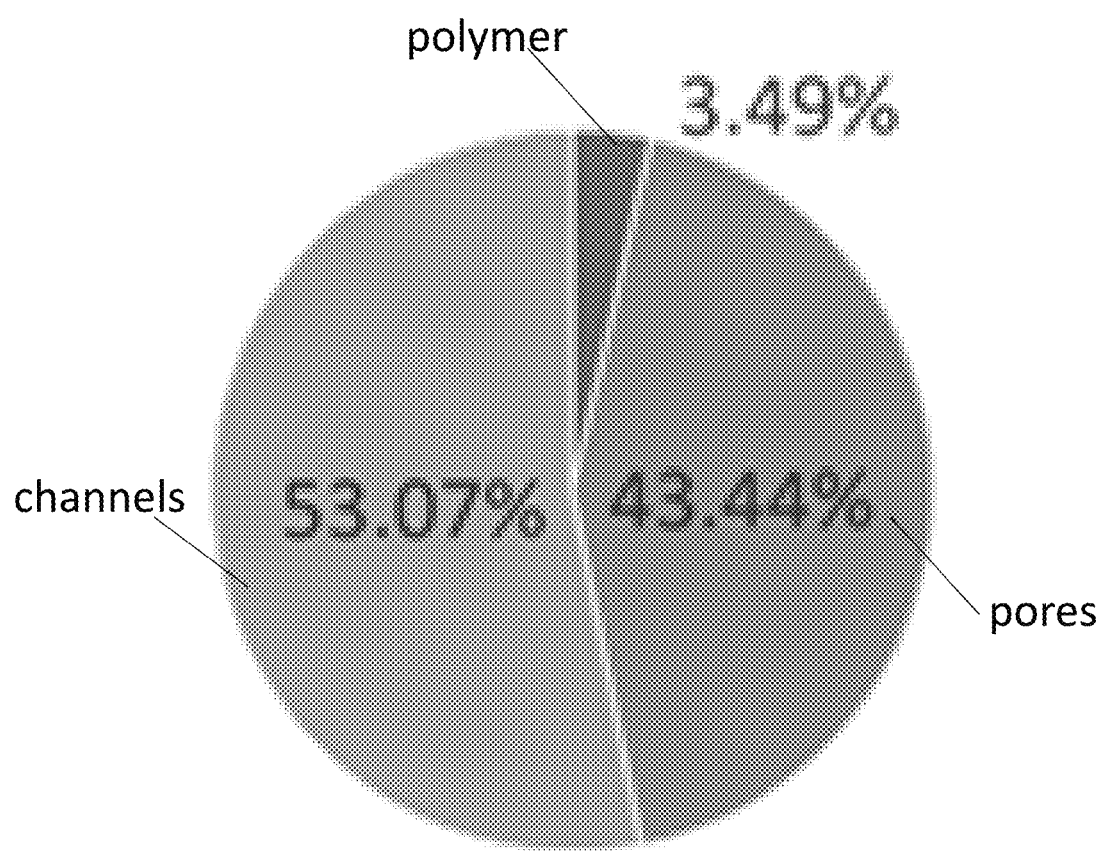
Figure 3J:
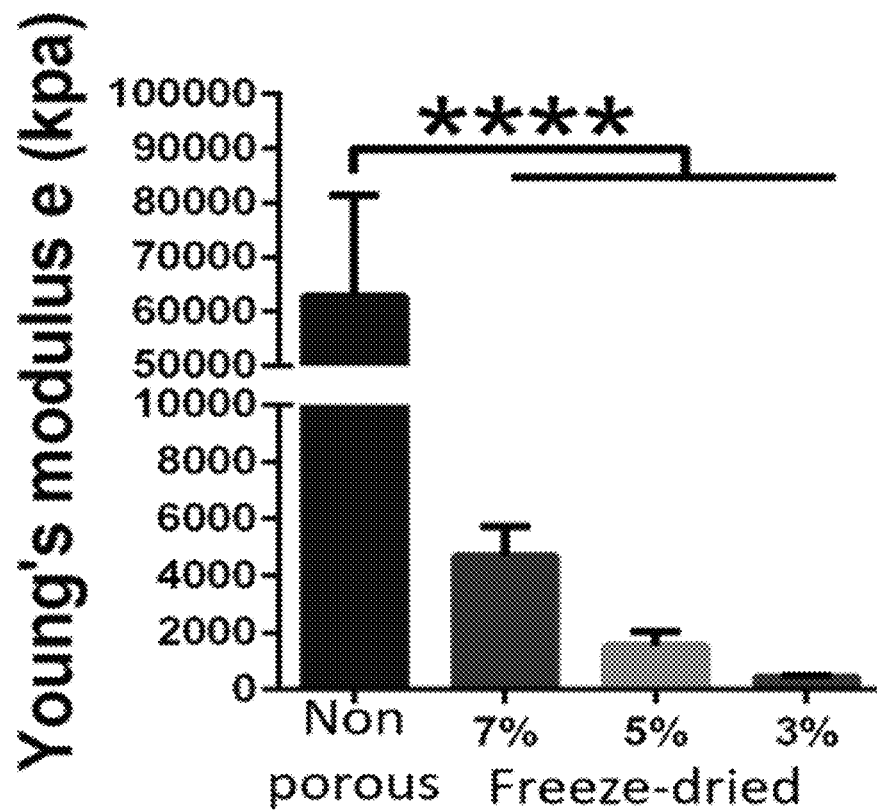

Graphs of the pore distribution by diameter are presented in FIGS. 3F-G and porosity measurements are presented in FIG. 3H.

Example 3

In Vitro Cell Culturing

Figure 4A:
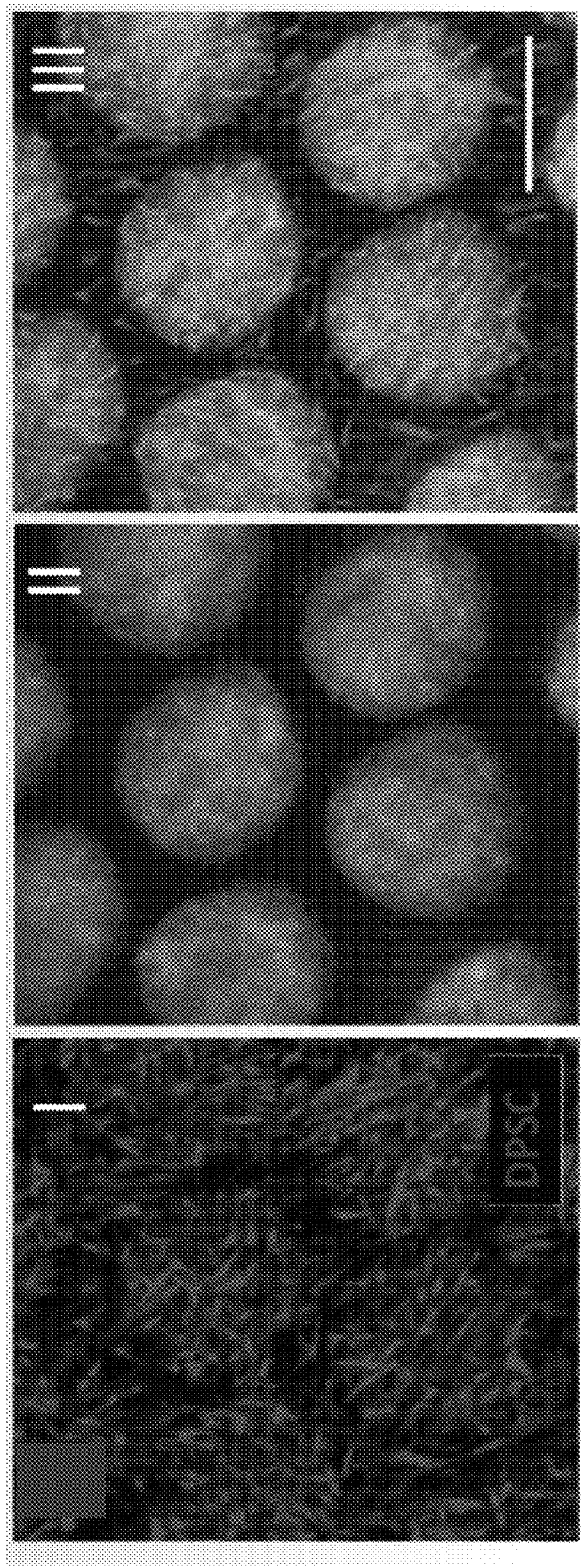
Figure 4B:
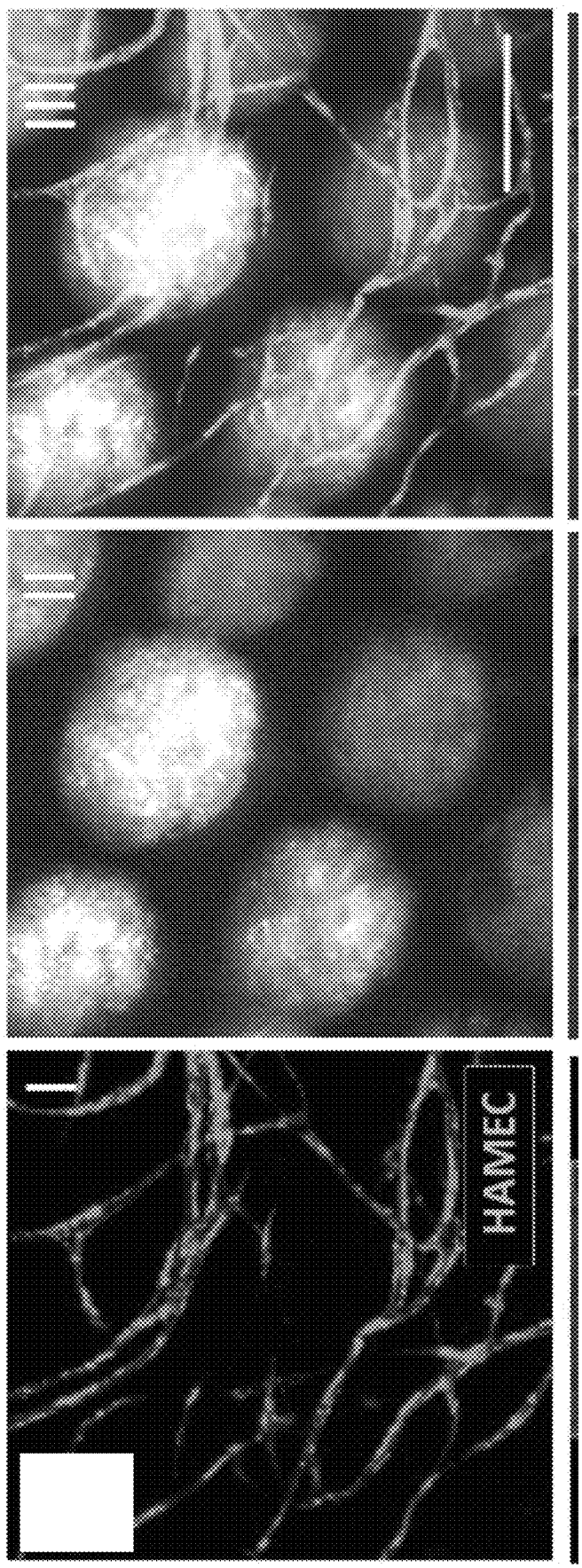
Figure 4C:
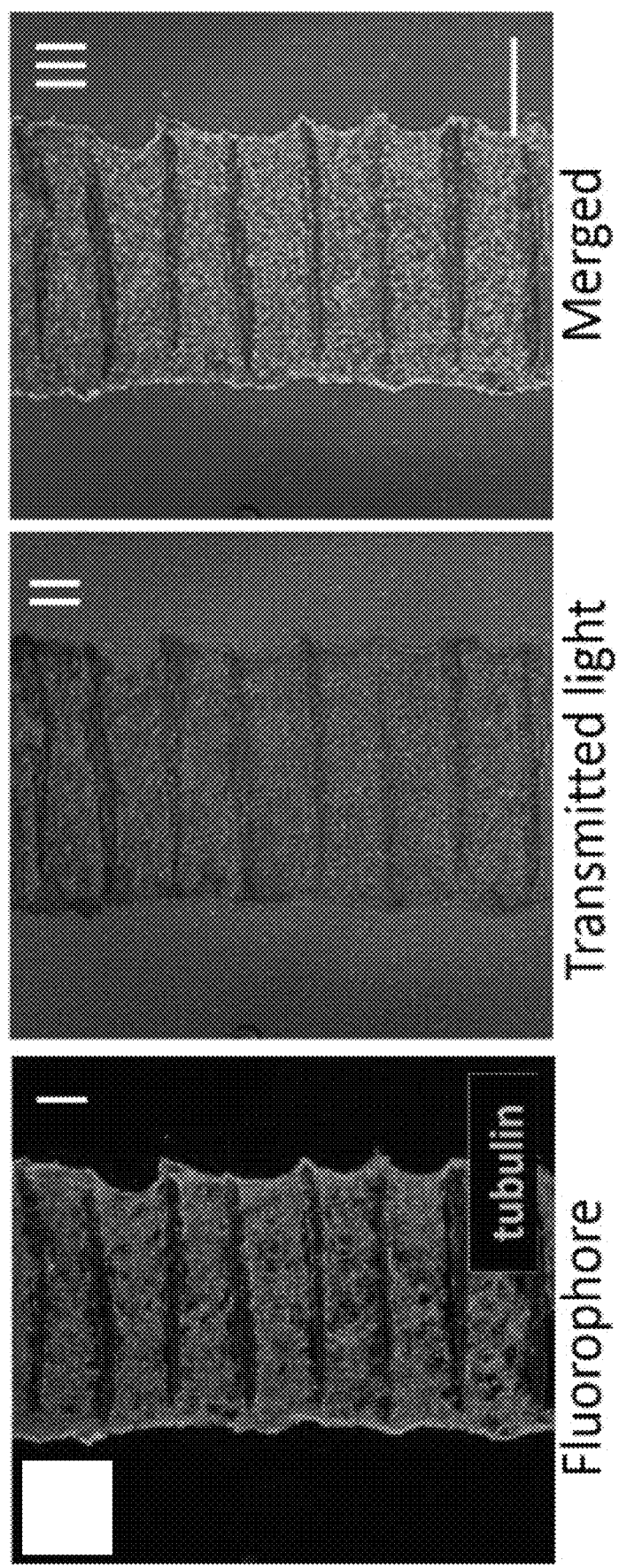

FIGS. 4A-D present pictures of Dental pulp stem cells (DPSC) growth (FIG. 4A), engineered blood vessels cultured on scaffold (FIG. 4B), and Induced pluripotent stem cell derived neurons (iPSC) fill channels (FIG. 4C). On day 1, only several cells were attached to the scaffold walls. However, by day 7, cells had fully filled the microchannels, likely as a result of proliferation (FIG. 4A). The cells appeared in a spreading morphology, indicating adequate culture and attachment conditions.

In FIG. 4D it can be seen scaffold supports neurite extension (II) compared with fibrin suspension alone. This is due to more effective diffusion in the scaffold (II) compared with fibrin suspension alone (I). Compared with fibrin plugs, neurons in scaffolds extended significantly more neurites as quantified by neurite number, total neurite length and neurite area.

Iodine diffusion into scaffolds and hydrogel plugs was also examined by employing μCT scanning under parameters that did not enable detection of porous PLLA/PLGA but did enable detection of iodine. Large non-diffusive core regions in fibrin plugs were observed (FIG. 4E-I), whereas in scaffolds, iodine penetrated deeper despite their greater thickness as compared to plugs (FIG. 4E-II). Yellow staining marks areas where diffusion is effective. This was likely due to a higher tissue density in the plugs as a result of engineered tissue contraction and could possibly indicate that nutrients and growth factors also limitedly diffused into the cores of the fibrin plugs. These observations indeed indicate that the porous microchannel scaffold provides more adequate growth conditions compared with regular hydrogel suspensions for the purpose of engineering neuronal tissues. Therefore, the reported scaffold could be used in various types of in vitro 3D tissue models for improved axonal growth.

The scale bar indicates 200 μm in A and B, 500 μm in C and 50 μm in D.

Example 4

In Vivo Studies

Figure 5C:
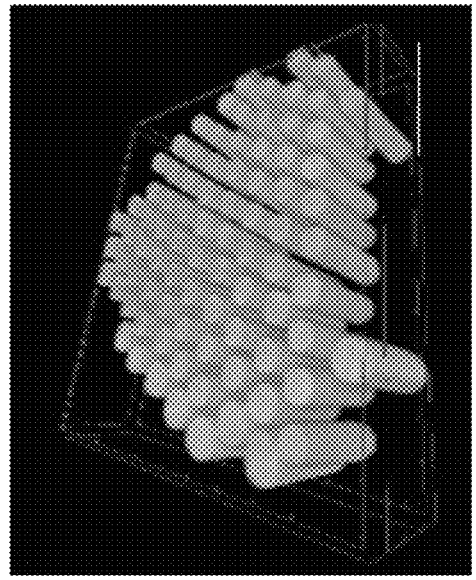
FIGS. 5A-5G present pictures of MRI scan of injured spinal cord for anatomical reconstruction of patterned scaffold (FIG. 5A), computer aided design of 3D reconstruction from injury site (FIG. 5B), uCT scan of anatomical BVOH construct (FIG. 5C), uCT scan of anatomical scaffold (FIG. 5D), complete spinal cord transection model implanted with scaffold of the invention (FIG. 5E), Host axons regenerate into scaffold of the invention (FIG. 5F), and stem cell derived axon in scaffold of the invention (FIG. 5G); scale bar indicates 500 μm in C and 1 mm in D, E and F.
Figure 5B:
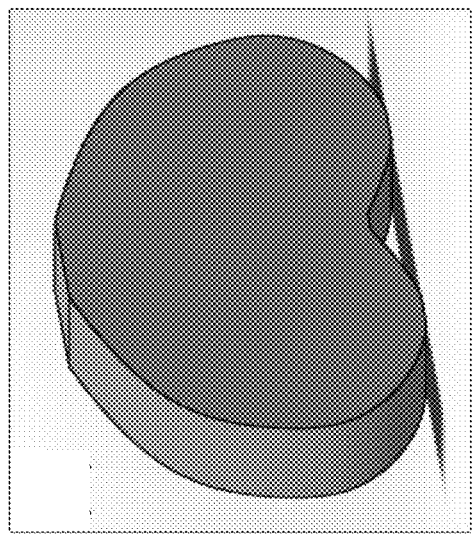
Figure 5A:
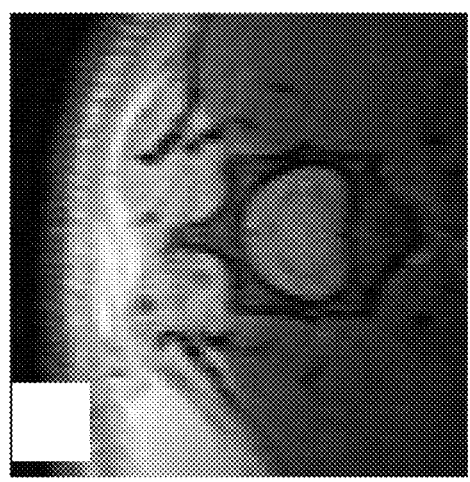

FIG. 5A presents pictures of MRI scan of injured spinal cord for anatomical reconstruction of patterned scaffold. Computer aided design of 3D reconstruction from injury site is presented in FIG. 5B, uCT scan of anatomical BVOH construct presented in FIG. 5C, uCT scan of anatomical scaffold presented in FIG. 5D.

Finally, the effect of the porous microchannel scaffold on guidance of grafted neurons was examined. Engineered neuronal tissues grown in porous microchannel scaffolds were implanted to sites of complete spinal cord injury (SCI).

Figure 5G:
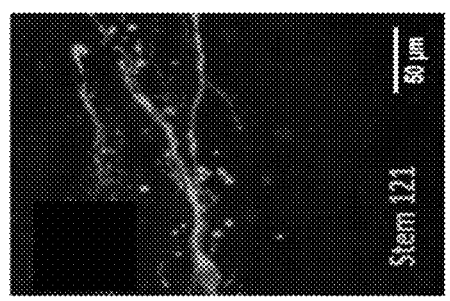
Figure 5F:
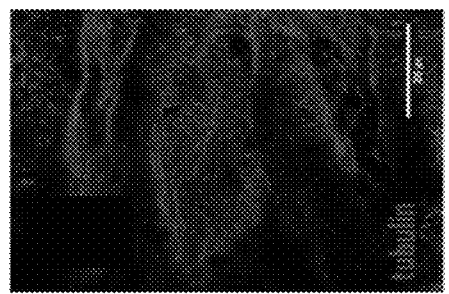
Figure 5E:
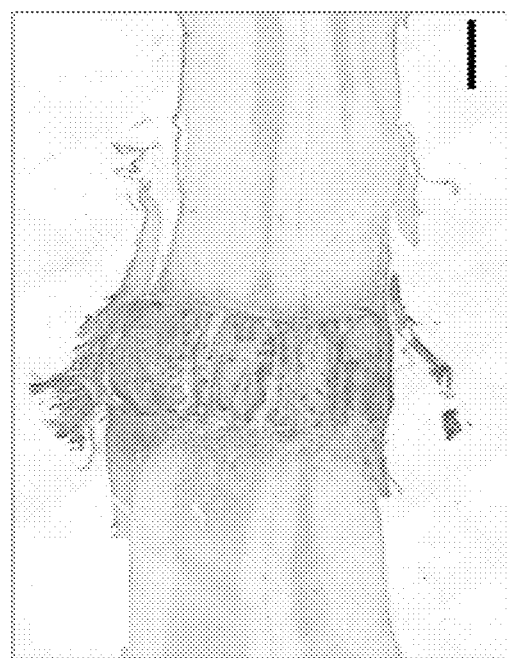
Figure 5D:
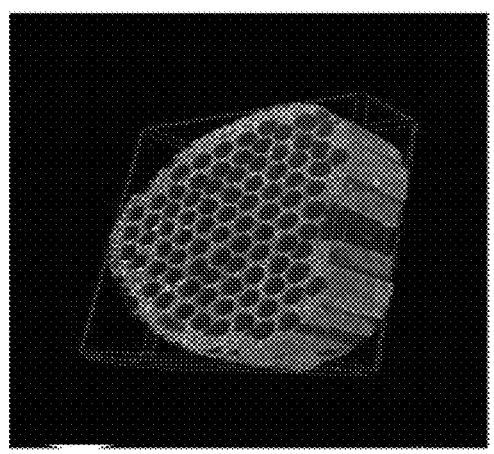

Complete spinal cord transection model implanted with scaffold is presented in FIG. 5E, Host axons regenerate into scaffold in FIG. 5F, and Stem cell derived axon in scaffold in FIG. 5G. The scale bar indicates 500 μm in C and 1 mm in D, E and F.

Figure 4F:
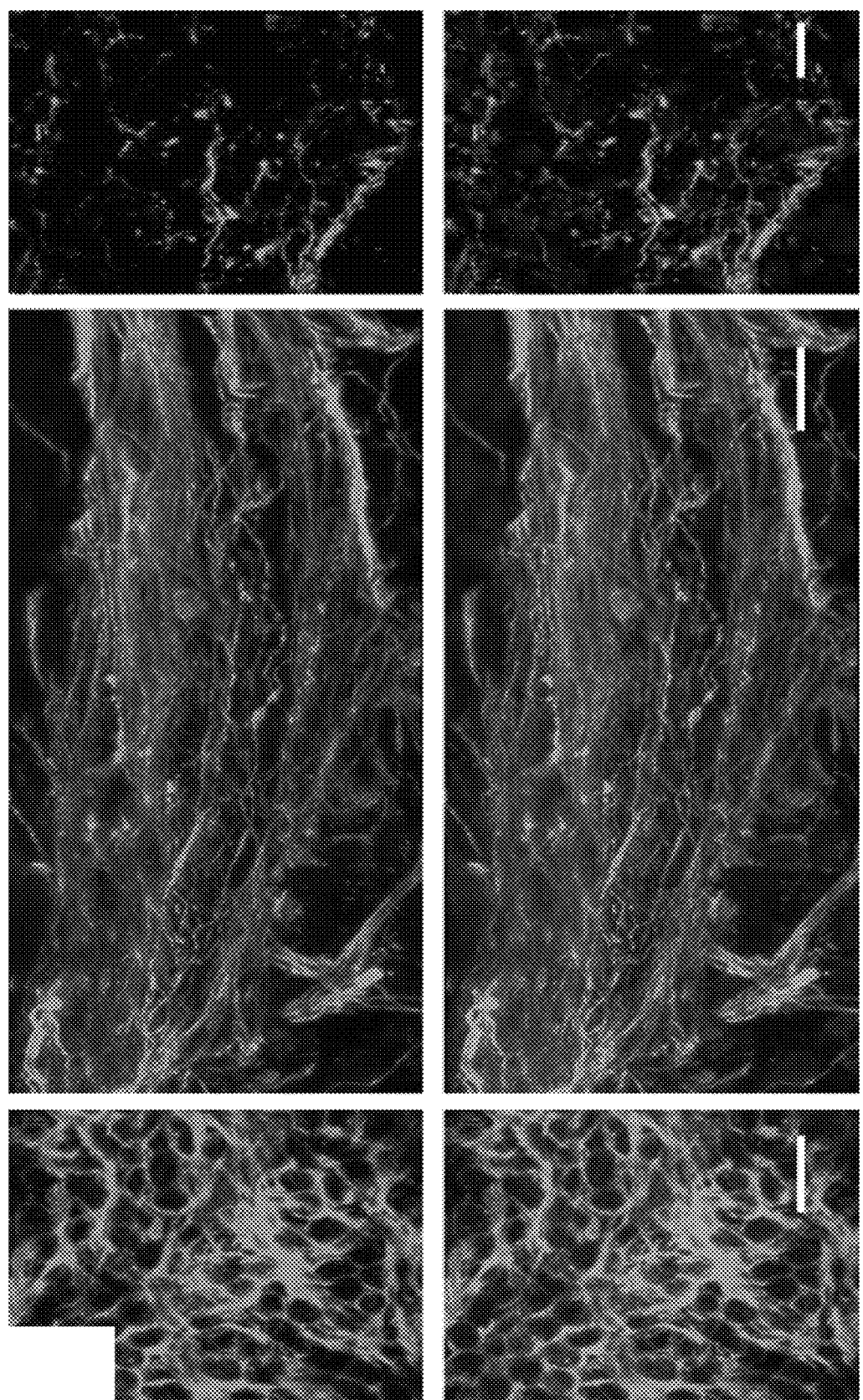

Two weeks post-implantation, survival of human cells in the lesion site was observed, as indicated by stem 121 antibody for human cytoplasm (FIG. 5G). Stem 121 staining consistently colocalized with $\beta_{III}$ tubulin, confirming that the cells are neurons. Importantly, Stem 121 positive regions inside microchannels appeared to bear two distinct morphologies, either as cell body clusters or extending axon fascicules originating from cell clusters (FIG. 4F). Stem cell-derived axons were also observed to project below the lesion site to the host spinal cord. Like regenerating host axons, human axons in extending fasciculus demonstrated a highly linear organization parallel to the microchannel direction with 83±4% of axons projecting in the range of ±20 degrees from the longitudinal axis of the scaffold (FIG. 4F). However, neurites in cell body clusters demonstrated a far less linear growth pattern with only 40±3% of neurites growing in the range of ±20 degrees from the longitudinal axis of the scaffold.

Axonal sensing of the engineered topography is possibly mediated by stromal or glial cells of larger size compared with axons. However, it is also possible that axons successfully follow microchannel direction since they are part of larger fasciculus where axon-to-axon interactions are present. These fascicules are often similar in diameter to the microchannels used in the current invention. This might explain the observed neurite orientation in stem cell-derived cell body clusters, which was less linear, possibly since axons were still not fully arranged in fascicules.

Figure 6A:
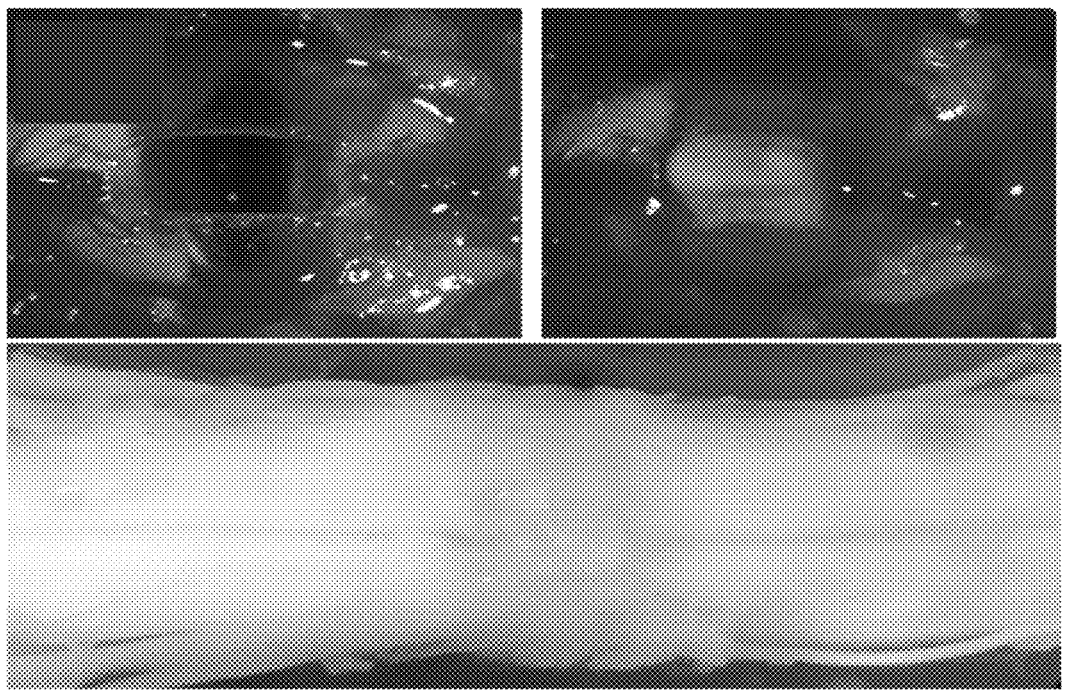
FIGS. 6A-6I present micrographs showing scaffold of the invention integration in vivo.
Figure 6B:
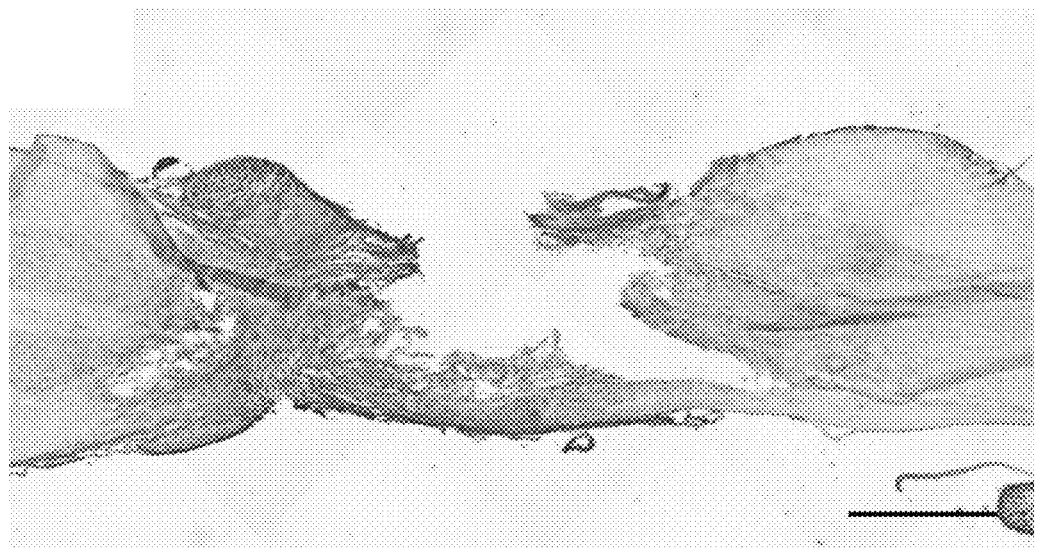
Figure 6C:
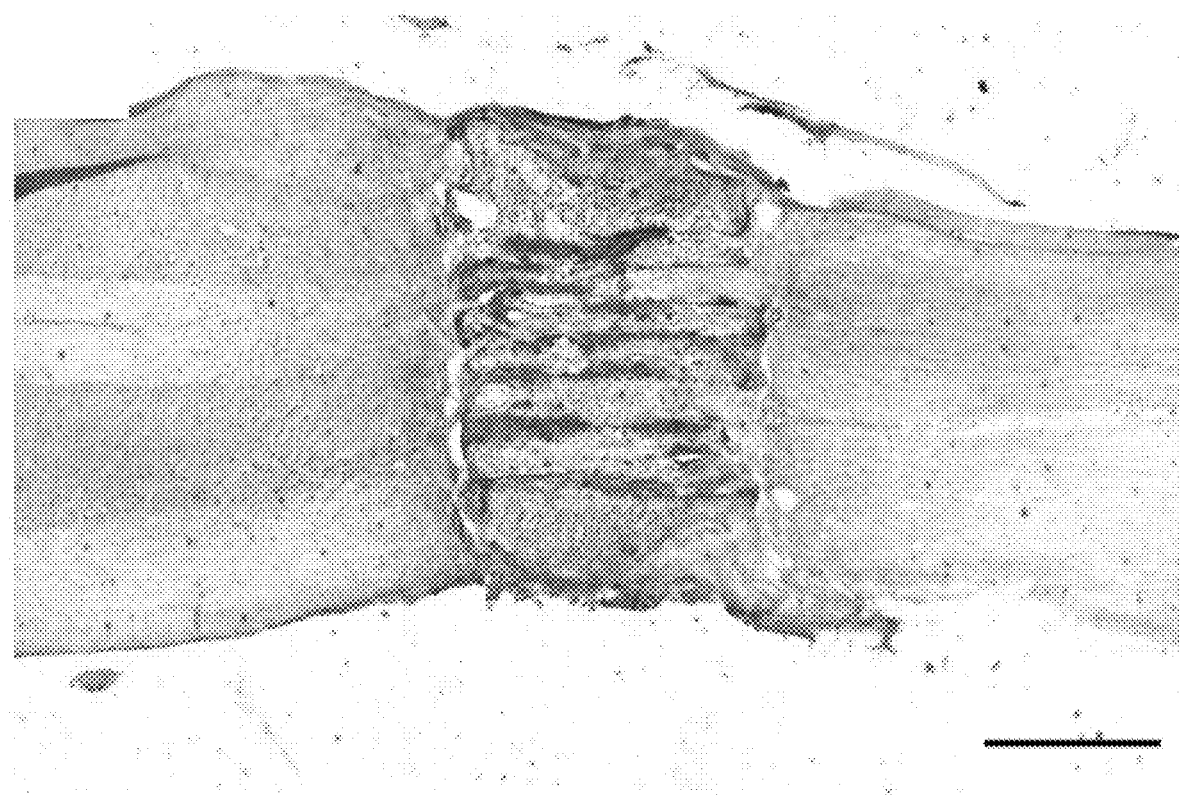
Figure 6D:
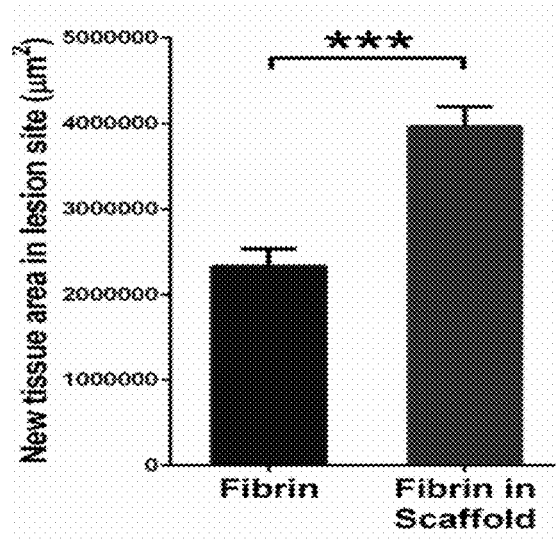
Figure 6I:
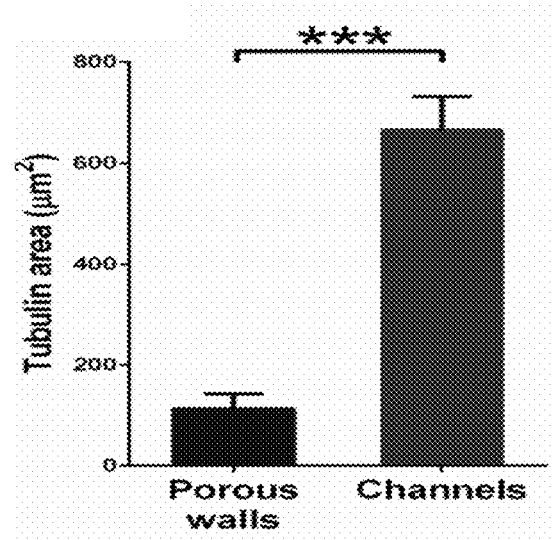
Figure 6E:
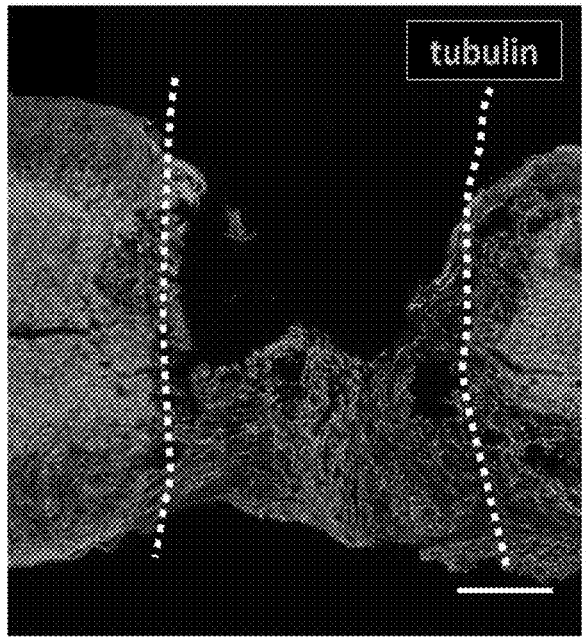
Figure 6F:
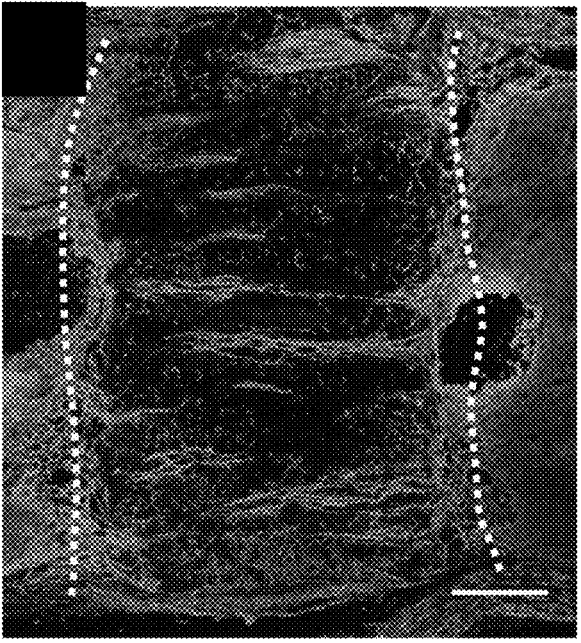
Figure 6G:
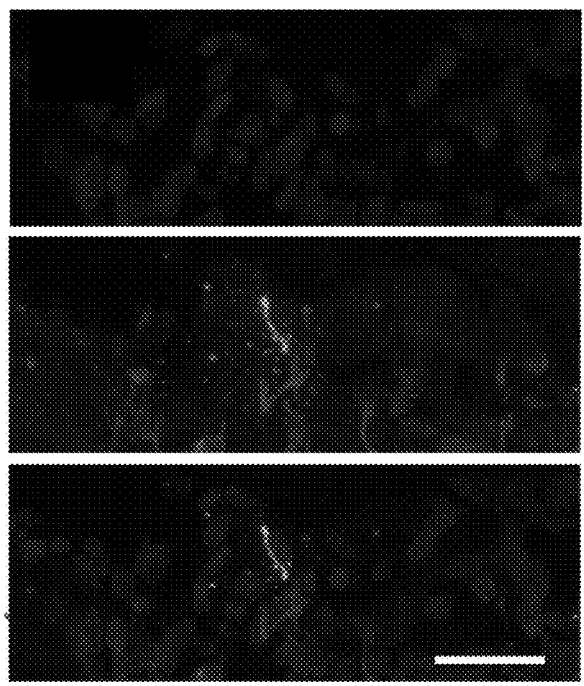
Figure 6H:
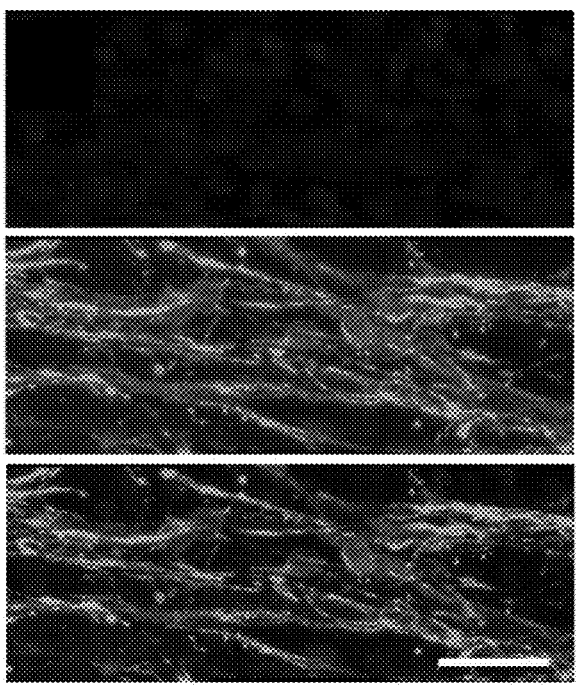

To evaluate the scaffold's axon regeneration-supporting capacities, fibrin-loaded anatomical scaffolds were implanted into a complete T10 transection model in rats (FIG. 6A). To isolate the effect of the scaffold on regenerating axons, scaffolds were compared to a control group in which an equal amount of fibrin was injected to fill the lesion as previously performed to induce axonal regeneration. Four weeks post-implantation, scaffolds were observed facilitating bridging of the lesion site and significantly enhanced formation of new tissue between disconnected stumps, as compared to the control group (FIG. 6B-D). This difference was likely due to the relatively high in vivo degradation rate of fibrin compared to PLLA/PLGA. In both groups, regenerating axons, indicated by $\beta_{III}$ tubulin staining, were observed in the lesion (FIG. 6E-F). As represented hereinabove, host cells penetrated both into the aligned microchannels and the porous walls of the scaffold. However, bundles of axons primarily regenerated into the aligned microchannels, and showed less penetration into the porous walls of the scaffold (FIGS. 6G-I).

Figure 7A:
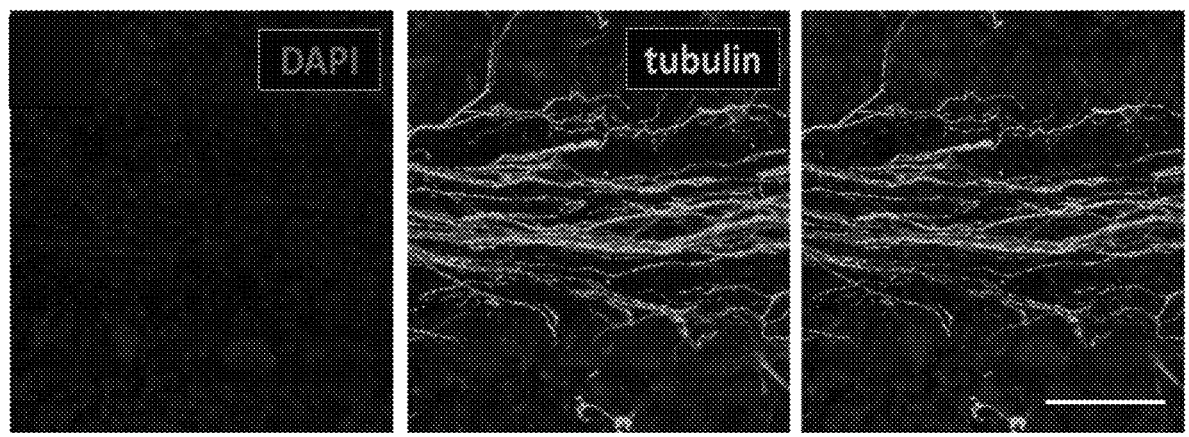
FIGS. 7A-7E present host axonal orientation in scaffold of the invention.
Figure 7B:
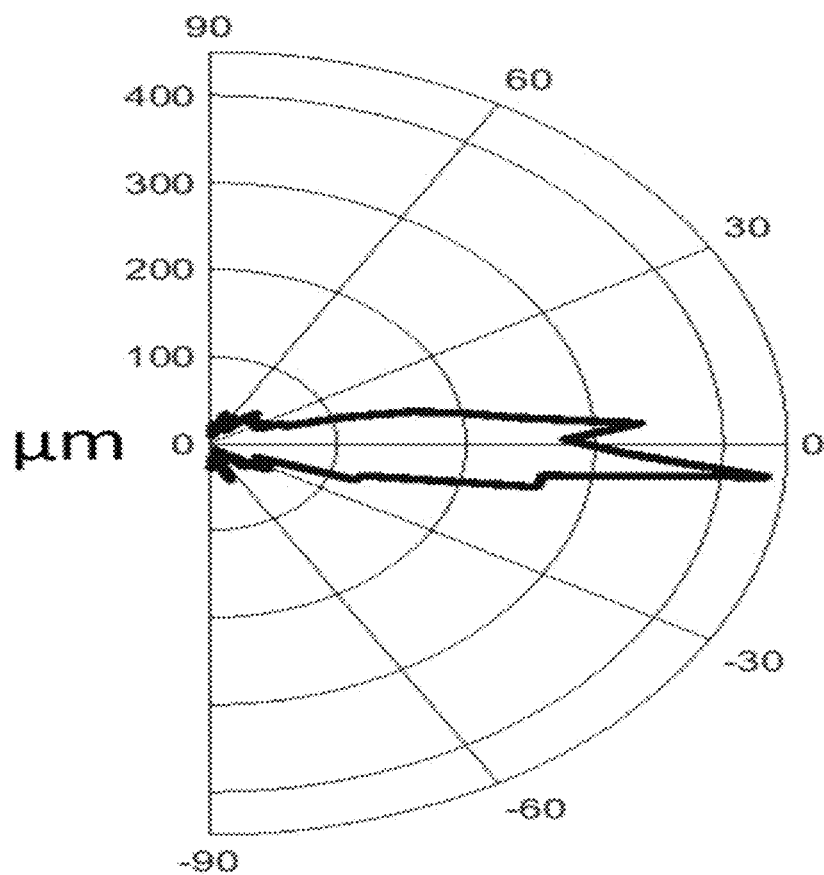
Figure 7C:
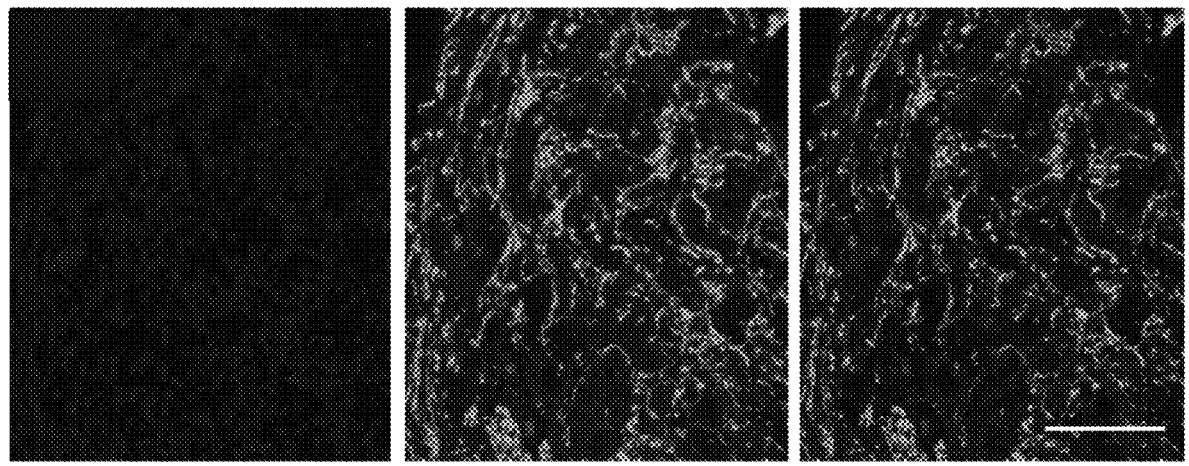
Figure 7D:
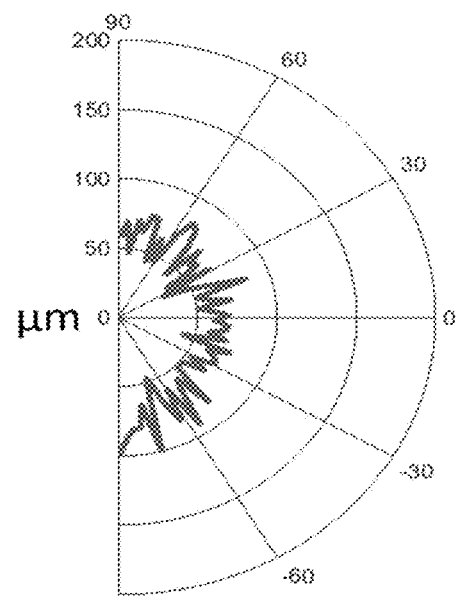
Figure 7E:
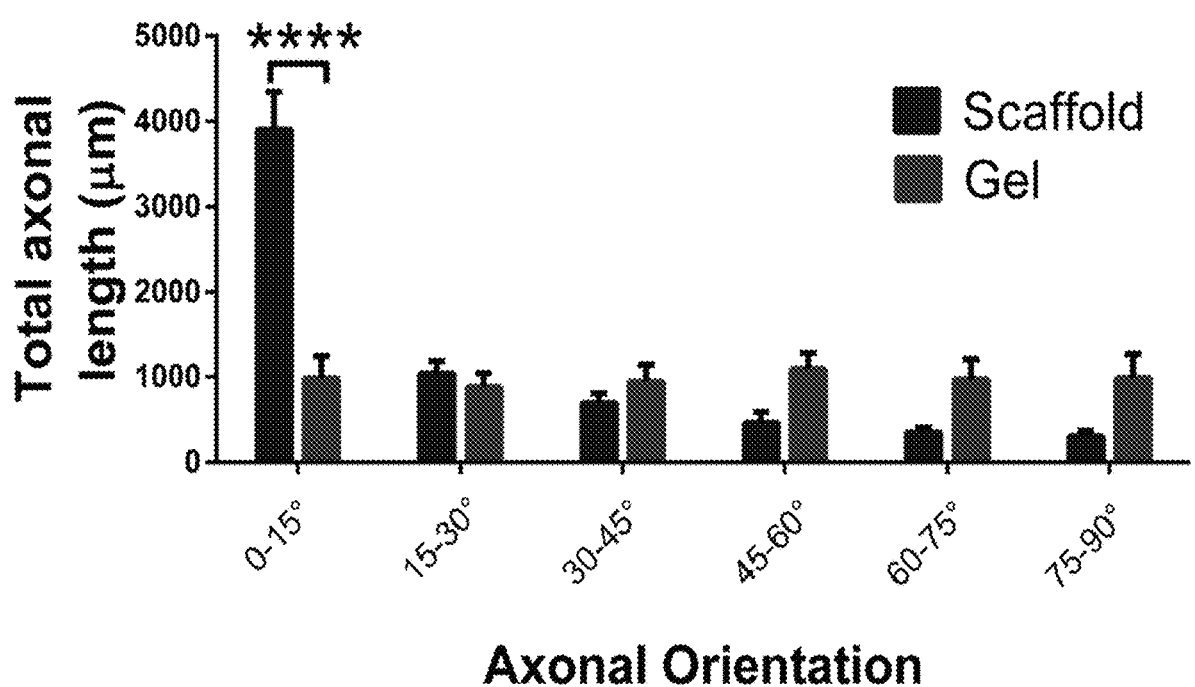

Since axons mostly regenerated into the aligned channels of the scaffold, an overall linear growth pattern was observed, resembling intact white matter axons (FIGS. 7A, B and E). In contrast, regenerating axons in control animals displayed a fully isotropic growth pattern (FIGS. 7C-E). These results demonstrate that the scaffold of the invention provides a suitable micro-architecture to guide linear axonal growth which failed to occur in the absence of the scaffold.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for making an implant scaffold, comprising:
   a. printing a 3D template comprising parallel linear structures aligned along a longitudinal axis of said 3D template; wherein the 3D template has a shape of a lesion site;
   b. contacting said 3D template with a solution comprising a polymeric precursor, thereby filling a space between the parallel linear structures in said 3D template;
   c. evaporating said solution, thereby obtaining an implant scaffold; and
   d. dissolving said 3D template; wherein said step a. comprises:
      printing a first layer comprising at least two linear anchors aligned along a transversal axis of said 3D template; and
      printing a second layer of said parallel linear structures, wherein each of the parallel linear structures bridges the at least two linear anchors.

2. The method of claim 1, wherein said printing the second layer comprises extruding a resin filament and simultaneously solidifying the extruded resin filament.

3. The method of claim 1, wherein said parallel linear structures are in a form of cylinders.

4. The method of claim 2, wherein said solidifying is performed by cold convection drying.

5. The method of claim 1, wherein an average cross-section of said parallel linear structures is in the range of 50 μm to 400 μm.

6. The method of claim 1, wherein a distance between two adjacent parallel linear structures is in the range of 5 μm to 150 μm.

7. The method of claim 1, wherein a material of said 3D template is a water-soluble material.

8. The method of claim 7, wherein the water-soluble material comprises butenediol vinyl alcohol (BVOH), polyvinyl alcohol (PVA), sucrose, lactose, sophorose, or any combination thereof.

9. The method of claim 1, wherein said solution comprises an organic solvent and wherein said polymeric precursor is soluble in said organic solvent.

10. The method of claim 9, wherein the concentration of said polymeric precursor in said solution is 1% to 50% (w/v %), and wherein said polymeric precursor is selected from the group consisting of poly(lactic-co-glycolic acid), poly (lactic acid), poly(glycolic acid), polycaprolactone, polydioxanone, PVA, polyurethanes, polycarbonates, polyhydroxyalkanoates (polyhydroxybutyrates and polyhydroxyvalerates and copolymers), polysaccharides, polyhydroxyalkanoates polyglycolide-co-caprolactone, polyethylene oxide, polypropylene oxide, polyglycolide-co-trimethylene carbonate, or combinations thereof.

11. The method of claim 1, wherein said evaporating is by freeze drying, and wherein the implant scaffold has a porosity of more than 90%.

\* \* \* \* \*